United States Patent
Sakata et al.

(10) Patent No.: US 6,562,808 B1
(45) Date of Patent: *May 13, 2003

(54) 5,11-DIHYDRODIBENZO[B,E][1,4] OXAZEPINE DERIVATIVES AND PHARMACEUTICAL COMPOSITION CONTAINING THE SAME

(75) Inventors: Katsutoshi Sakata, Kawasaki (JP); Takashi Tsuji, Kawasaki (JP); Noriko Sasaki, Kawasaki (JP); Kazuyoshi Takahashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/522,946

(22) Filed: Mar. 10, 2000

Related U.S. Application Data

(63) Continuation of application No. PCT/JP98/04071, filed on Sep. 10, 1998.

(30) Foreign Application Priority Data

Sep. 10, 1997 (JP) .............................. 9-245669
Sep. 10, 1997 (JP) .............................. 9-245670

(51) Int. Cl.$^7$ ........................ A61K 31/553; A61P 1/00; C07D 267/18
(52) U.S. Cl. ..................... 514/211.1; 540/550
(58) Field of Search ................ 514/211.11; 540/550

(56) References Cited

U.S. PATENT DOCUMENTS

| 5,071,844 A | | 12/1991 | Alker et al. ................. 514/211 |
| 5,449,674 A | | 9/1995 | Hagen et al. ................ 514/211 |
| 6,127,361 A | * | 10/2000 | Tanaka et al. ........... 514/211.11 |

FOREIGN PATENT DOCUMENTS

| EP | 0 404 359 | 12/1990 |
| JP | 3-17079 | 1/1991 |
| JP | 7-501054 | 2/1995 |
| WO | WO 93/09104 | 5/1993 |
| WO | 97/33885 | 9/1997 |

* cited by examiner

Primary Examiner—Bruck Kifle

(57) ABSTRACT

5,11-dihydrodibenzo[b,e][1,4]oxazepine derivatives of the following general formulae and analogs thereof have a calcium channel-antagonistic effect and they are effective in treating and preventing intestinal diseases such as abnormal motor function of digestive tracts, particularly, irritable bowel syndrome:

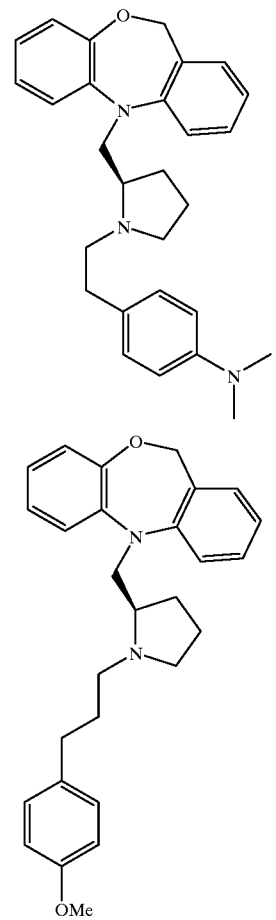

49 Claims, No Drawings

5,11-DIHYDRODIBENZO[B,E][1,4] OXAZEPINE DERIVATIVES AND PHARMACEUTICAL COMPOSITION CONTAINING THE SAME

This application is a Continuation-in-part (CIP) of International Application No. PCT/JP98/04071, filed Sep. 10, 1998.

BACKGROUND OF THE INVENTION

The present invention relates to 5,11-dihydrodibenzo[b, e][1,4]oxazepine derivatives, stereoisomers thereof, pharmacologically acceptable salts thereof and hydrates of them having a calcium channel-antagonistic effect and effective in treating and preventing intestinal diseases such as abnormal motor function of digestive tracts, particularly, irritable bowel syndrome, as well as pharmaceutical compositions containing them.

It is disclosed in, for example, European Patent No. 0404359A1 that 5,11-dihydrodibenzo[b,e][1,4]thiazepine derivatives are useful as calcium channel antagonists selectively effective on gastrointestinal tracts. In addition, Quinn P. et al and Wallis R. M. et al. also disclosed in Brit. J. Pharmacol. 1994, 112 (Suppl.), Abst 573P and Brit. Pharmacol. 1994, 112 (Suppl.) Abst 574P, respectively, that (S)-5-[1-(4-methoxyphenyl)ethyl]pyrrolidine-2-ylmethyl]-5,11-dihydrodibenzo[b,e][1,4]thiazepine maleate has the same effect as that described above. However, one of the defects of these compounds is that they have anticholinergic effect to cause side effects such as thirst and mydriasis.

As the social environment has become increasingly complicated, many people have been exposed to severe stress, and patients having irritable bowel syndrome mainly with irregular bowel movement and abdominal pain are increasing in number. Drugs given to the patients of such diseases include anticholinergics, laxatives, antidiarrheal drugs, intestinal drugs, mucosal paralyzing agents, drugs for controlling motor function of digestive tracts, autonomic drugs, Chinese orthodox medicines, antianxiety drugs, antidepressants, sleep promoting drugs and antipsychotic agents. However, the clinical effects of these drugs are yet insufficient and the drugs are not always satisfactory in view of their side effects. Under these circumstances, the development of a new-type drug having an excellent effect of improving the motor function of digestive tracts is demanded.

SUMMARY OF THE INVENTION

An object of the present invention is to provide new compounds having an excellent effect of improving the motor function of digestive tracts.

Another object of the present invention is to provide a pharmaceutical composition containing such new compounds.

Other objects of the present invention will be apparent from the following description and Examples given below.

It is generally considered that calcium channel antagonists are effective in treating intestinal diseases caused by abnormal acceleration of the contraction of intestinal tracts such as irritable bowel syndrome because they have a function of inhibiting the contraction of the smooth muscles. In fact, it was reported that calcium channel antagonists such as Nicardipine and Verapamil are effective on irritable bowel syndrome [Am. J. Gastroenterol., 80, 317 (1985); Gut. 28 1609 (1987); J. Clin. Psychiatry., 48, 388 (1987); an Pharmacol. Ther., 60, 121 (1993)]. However, these antagonists are rarely used clinically at present because of the main effects of the calcium channel antagonists on the cardiovascular system. Under these circumstances, the inventors made intensive investigations for the purpose of developing a calcium channel antagonist with low toxicity which is ineffective on the cardiovascular system but which is selectively effective on the intestinal tracts and is usable as a drug for abnormal motor function of intestinal tracts, particularly irritable bowel syndrome. After the investigations, the inventors have found that compounds represented by the following general formula [I-I] or [I-II] have calcium channel antagonistic activity selectively on the intestinal tracts and that they are usable as remedies for abnormal motor function of digestive tracts. The present invention has been completed on the basis of this finding.

Namely, the present invention relates to 5,11-dihydrodibenzo[b,e][1,4]oxazepine derivatives represented by the following general formula [I-I] or [I-II], stereoisomers thereof, pharmacologically acceptable salts thereof and hydrates of them; and pharmaceutical compositions containing them as active ingredients, particularly pharmaceutical compositions for treating or preventing abnormal motor function of intestinal tracts:

[I-I]

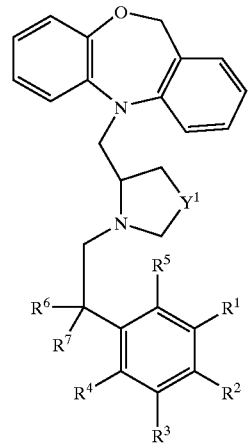

wherein $R^1$ through $R^5$ may be the same or different from one another and they each represent a hydrogen atom, lower alkoxyl group, amino group or alkylamino group with the proviso that at least one of them represents the amino group or alkylamino group; $R^6$ and $R^7$ may be the same or different from one another and they each represent a hydrogen atom or hydroxyl group, or they together form =O; and $Y^1$ represents a methylene group, sulfur atom or hydroxymethine group;

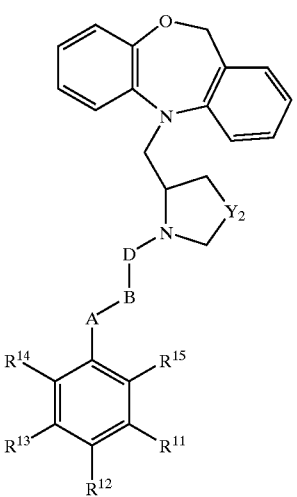

wherein $R^{11}$ through $R^{15}$ may be the same or different from one another and they each represent a hydrogen atom, halogen atom, cyano group, hydroxyl group, lower alkoxyl group, amino group or alkylamino group, or $R^{15}$ and $R^{11}$, $R^{11}$ and $R^{12}$, $R^{12}$ and $R^{13}$ or $R^{13}$ and $R^{14}$ together form —O(CH$_2$)$_n$O— group (n being 1, 2 or 3); $Y^2$ represents a methylene group, sulfur atom or hydroxymethine group; A represents CH$_2$, CHOH, CO or O, B represents CH$_2$ or CHOH; or A—B represents CH=CH and D represents CH$_2$, CH$_2$—CH$_2$ or CH$_2$—CH$_2$—CH$_2$.

DESCRIPTION OF THE PREFERRED EMBODIMENTS

The lower alkoxyl groups represented by $R^1$ through $R^5$ in above general formula [I-I] are preferably those having 1 to 5 carbon atoms, and more preferably those having 1 to 3 carbon atoms. The alkylamino groups represented by $R^1$ through $R^5$ include monoalkylamino groups and dialkylamino groups. The alkyl groups are preferably those having 1 to 5 carbon atoms and more preferably those having 1 to 3 carbon atoms.

In the present invention, it is preferred that one of $R^1$ through $R^5$ is an amino group or alkylamino group, and the balance is hydrogen atom. Further, in this case, $R^6$ and $R^7$ are each hydrogen atom. $Y^1$ is preferably methylene group.

$R^1$ and $R^2$ may be the same or different from each other and they each represent a hydrogen atom, amino group or alkylamino group in the present invention. It is preferred that $R^1$ and $R^2$ do not represent hydrogen atom at the same time and $R^3$, $R^4$ and $R^5$ are each hydrogen atom. It is preferred in the present invention that both $R^1$ and $R^2$ represent an amino group or alkylamino group, and it is more preferred that one of $R^1$ and $R^2$ represents an amino group or alkylamino group and the other represents a hydrogen atom. It is also preferred that one of $R^1$ and $R^2$ represents an amino group or alkylamino group and the other represents a lower alkoxyl group. It is particularly preferred that $R^2$ represents an amino group or alkylamino group, and $R^1$ represents a hydrogen atom.

It is preferred in the present invention that $R^6$ and $R^7$ in general formula [I-I] each represent a hydrogen atom and $Y^1$ represents methylene group. In these compounds, particularly preferred compounds are those represented by the following formulae, i.e. (R)-5,11-dihydro-5-[1-[2-(4-dimethylaminophenyl)ethyl]-2-pyrrolidinylmethyl]dibenzo[b,e][1,4]oxazepine, (R)-5,11-dihydro-5-[1-[2-(4-diethylaminophenyl)ethyl]-2-pyrrolidinylmethyl]dibenzo[b,e][1,4]oxazepine, (R)-5,11-dihydro-5-[1-[2-(3-dimethylaminophenyl)ethyl]-2-pyrrolidinylmethyl]dibenzo[b,e][1,4]oxazepine, (R)-5,11-dihydro-5-[1-[2-(3-methylaminophenyl)ethyl]-2-pyrrolidinylmethyl]dibenzo[b,e][1,4]oxazepine and (R)-5,11-dihydro-5-[1-[2-(2-dimethylaminophenyl)ethyl]-2-pyrrolidinylmethyl]dibenzo[b,e][1,4]oxazepine, as well as pharmaceutically acceptable salts thereof and hydrates of them.

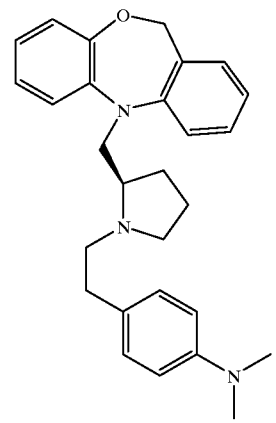

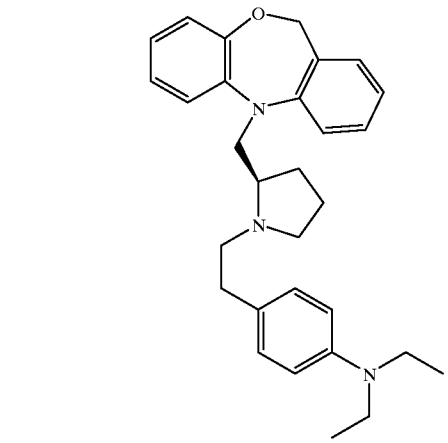

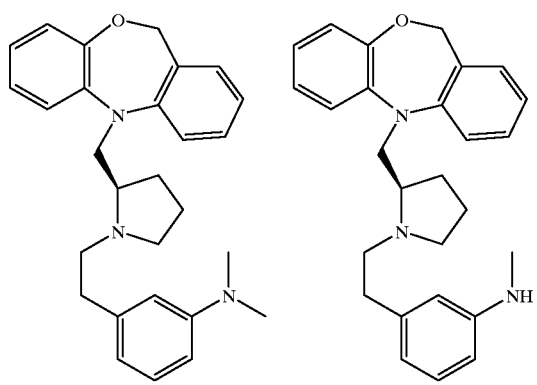

-continued

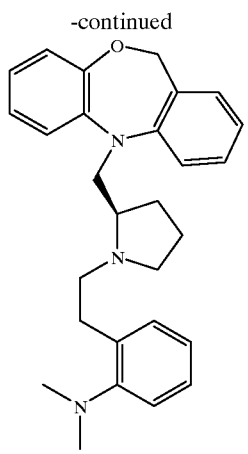

Compounds [I-I] of the present invention can be produced by, for example, following method A-1:

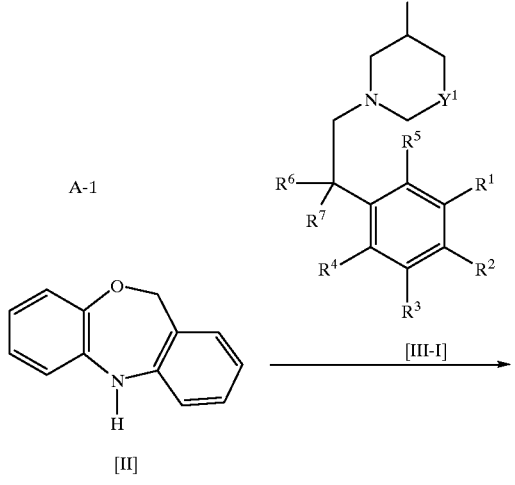

wherein $R^1$ through $R^7$ and $Y^1$ are as defined above, and $X^1$ represents chlorine atom, bromine atom or iodine atom. It is preferred that $R^6$ and $R^7$ are each a hydrogen atom, and $Y^1$ is methylene group.

Compounds [I-I] of the present invention can be produced by reacting a compound [II] with a halide represented by above general formula [III-I] in the presence of a base in a solvent.

The reaction solvents include amides such as N,N-dimethylformamide; ethers such as tetrahydrofuran, diethyl ether, dioxane and 1,2-dimethoxyethane; acetonitrile; toluene; xylene; benzene and dimethyl sulfoxide. The bases include lithium carbonate, sodium carbonate, potassium carbonate, sodium hydride, potassium hydride, lithium diisopropylamide, n-butyllithium, sodium methoxide and potassium t-butoxide.

The reaction temperature is in the range of usually 0 to 150° C., preferably room temperature to 100° C.

The reaction time, which varies depending on the reaction temperature and the variety of the solvent, is usually 1 to 150 hours.

The amount of each of compound [III-I] and the base is at least one mol, preferably 1 to 5 mols, per mol of compound [II].

Compound [II] used as a starting material in the above-described reaction can be produced by a well-known method [J. Med. Chem., 7, 609 (1964)].

The halides represented by above general formula [III-I] can be produced from proline, hydroxyproline, and thioproline obtained by reacting cysteine with formaldehyde, by a known method [EPO 404359A1].

In method A-1, the stereochemical structures of the compounds of the present invention were determined according to a reaction mechanism described in literatures [[EPO 404359A1 and Tetrahedron, 37, 2173 (1981)].

Compounds [I-I] of the present invention can also be produced by following method B-1:

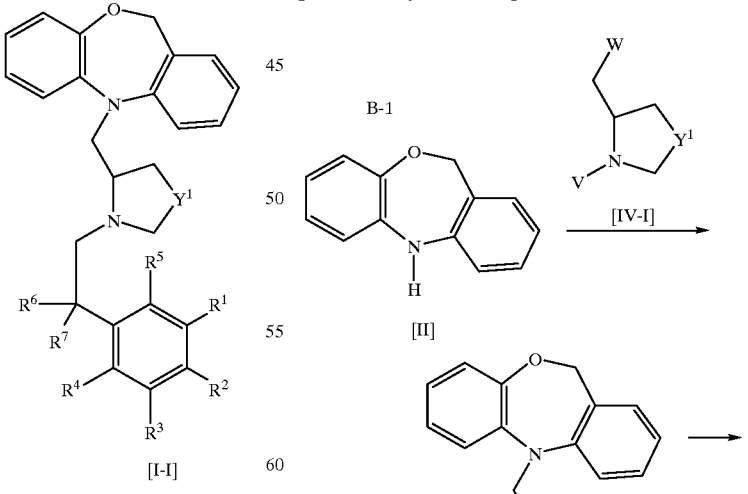

-continued

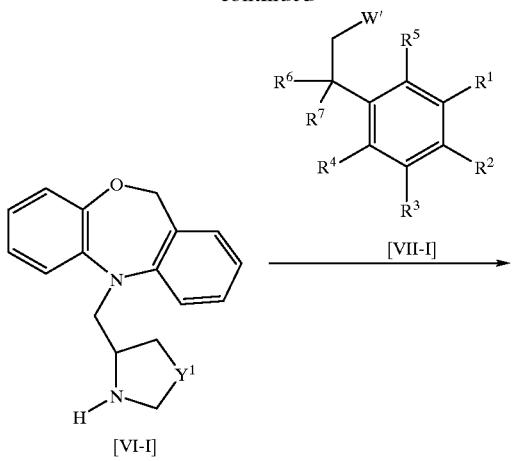

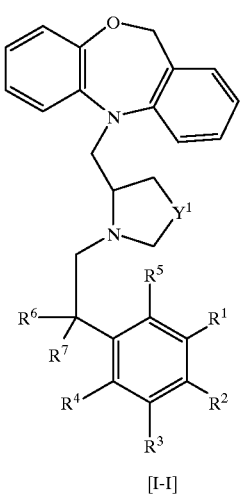

wherein $R^1$ through $R^7$ are as defined above, $Y^1$ represents methylene group, sulfur atom or hydroxymethine group, V represents a group for protecting the amino group such as t-butoxycarbonyl group, benzyloxycarbonyl group or tosyl group, and W and W' each represent a leaving group such as chlorine atom, bromine atom, iodine atom, mesyl group or tosyl group.

Compounds [I-I] of the present invention can be produced by dropping, for example, an N-t-butoxycarbonyl-2-pyrrolidinylmethyl tosylate of above general formula [IV-I] into compound [II] to conduct the reaction in a solvent and thereby to form a compound of general formula [V-I], removing the protecting group to obtain a compound of general formula [VI-I] and reacting this compound with a compound of general formula [VII-I] in the presence of a base.

The base and the reaction solvent used in this process may be the same as those used in above-described reaction A-1.

A compound [I-I] of the present invention, wherein any of $R^1$ through $R^5$ is an amino group or monoalkylamino group, can be produced by synthesizing a precursor, wherein the amino group or monoalkylamino group is protected with an amino group-protecting group such as t-butoxycarbonyl group, benzyloxycarbonyl group, tosyl group, benzyl group or trityl group, or a corresponding nitro compound by method A-1 or B-1; and then removing the protecting group or reducing the nitro compound to obtain the amino group or monoalkylamino group. Alkylamino compounds or dialkylamino compounds can also be obtained by N-alkylating corresponding amino compounds or monoalkylamino compounds.

C

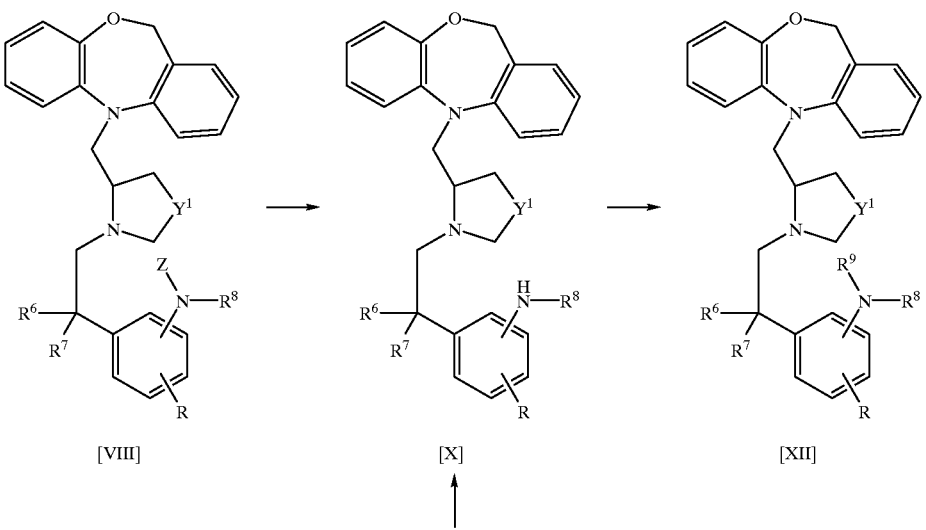

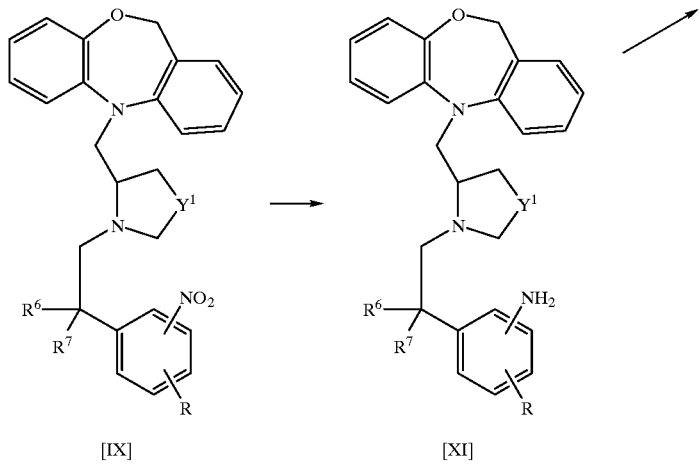

[IX]   [XI]

wherein R represents a hydrogen atom or lower alkoxyl group, $R^6$, $R^7$ and $Y^1$ are as defined above, $R^8$ and $R^9$ each represent a hydrogen atom or lower alkyl group, and Z represents an amino group-protecting group such as t-butoxycarbonyl group, benzyloxycarbonyl group, tosyl group, benzyl group or trityl group.

The protecting group is removed from compound [VIII] by an ordinary method to obtain compound [X] or compound [IX] is reduced by the catalytic hydrogenation or reduction with a metal to obtain compound [XI] which is then alkylated. Compounds [X] to [XII] are thus obtained. The alkylation can be easily conducted by using an ordinary alkylating agent such as an alkyl halide or alkyl tosylate, or by the reductive alkylation wherein the compound is condensed with a carbonyl compound and then the condensate is reduced. The dialkyl compounds can be obtained in two steps by producing compound [X] from compound [XI] and then converting the product into compound [XII]. When $R^8$ and $R^9$ are the same lower alkyl group, the compound can be directly converted into compound [XII] in one step.

In general formula [I-II], the halogen atoms of $R^{11}$ through $R^{15}$ include fluorine atom and chlorine atom; the lower alkoxyl groups include those having 1 to 5 carbon atoms such as methoxyl, ethoxyl and n-propoxyl groups; the alkylamino groups include monoalkylamino groups and dialkylamino groups; —$O(CH_2)_nO$— groups include methylenedioxy, ethylenedioxy and propylenedioxy groups. In the halogen atoms, fluorine atom is preferred; and in the lower alkoxyl groups, those having 1 to 3 carbon atoms are preferred. In the monoalkylamino groups and dialkylamino groups, those wherein the alkyl group has 1 to 5 carbon atoms are preferred and those wherein the alkyl group has 1 to 3 carbon atoms are more preferred. Particularly preferred are dialkylamino-groups).

A—B—D is preferably CHOH—$CH_2$—$CH_2$, $CH_2$—CHOH—$CH_2$, CH=CH—$CH_2$, CO—$CH_2$—$CH_2$, O—$CH_2$—$CH_2$ or $CH_2$—$CH_2$—$CH_2$.

In general formula [I], $Y^2$ is preferably methylene group, and $R^{11}$ through $R^{15}$ are not hydrogen atoms at the same time. $R^{11}$ and $R^{12}$ may be the same or different from each other and preferably, they each represent a hydrogen atom, halogen atom, cyano group, hydroxyl group, lower alkoxyl group, amino group or alkylamino group, $R^{13}$ through $R^{15}$ each represent a hydrogen atom, $R^{11}$ and $R^{12}$ together form —$O(CH_2)_nO$— group (n being 1, 2 or 3). Preferably $R^{11}$ represents hydrogen atom and $R^{12}$ represents a halogen atom or lower alkoxyl group. More preferably, $R^{12}$ represents a methoxyl group, and $R^{11}$ and $R^{13}$ through $R^{15}$ each represent hydrogen atom, or $R^{11}$ represents an amino group or alkylamino group, and $R^{12}$ through $R^{15}$ each represent hydrogen atom. In these compounds, particularly preferred compounds are (R)-5,11-dihydro-5-[1-[3-(4-methoxyphenyl)propane-1-yl]-2-pyrrolidinylmethyl]dibenzo[b,e][1,4]oxazepine, pharmacologically acceptable salts of them and hydrates of them:

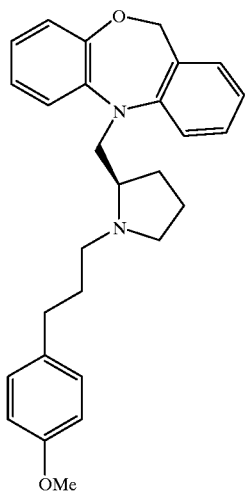

Compounds [I-II] of the present invention can be produced by, for example, following method A-2:

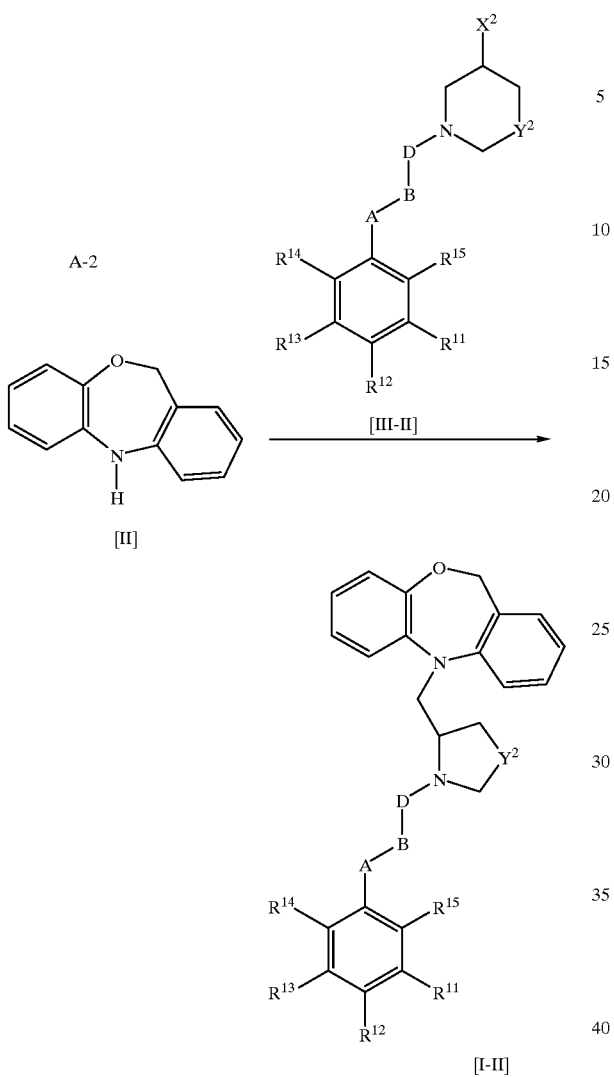

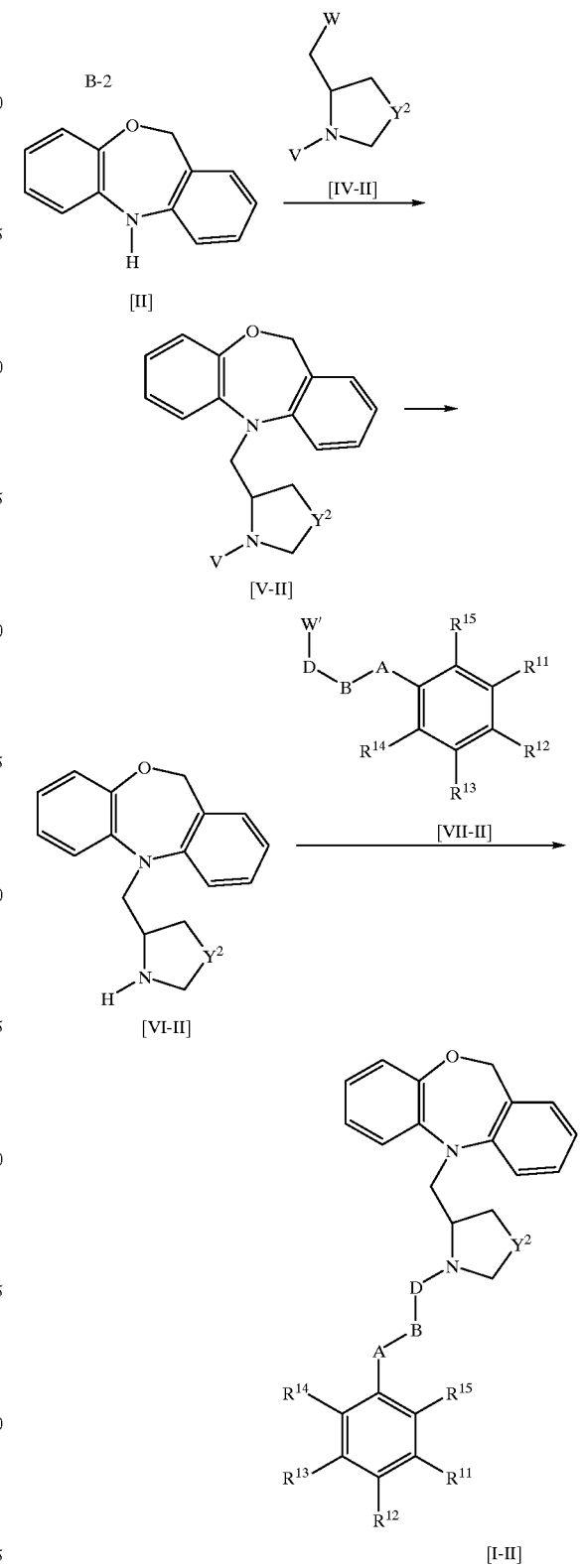

wherein $R^{11}$ through $R^{15}$, A, B, D and $Y^2$ are as defined above, and $X^2$ represents chlorine atom, bromine atom or iodine atom.

Compounds [I-II] of the present invention can be produced by reacting compound [II] with a halide represented by above general formula [III-II] in the presence of a base in a solvent.

The same reaction solvent and base as those used for the above-described reaction A-1 can be used for this reaction.

The reaction temperature is in the range of usually 0 to 150° C., preferably room temperature to 100° C.

The reaction time, which varies depending on the reaction temperature and the variety of the solvent, is usually 1 to 150 hours.

The amount of each of compound [III-II] and the base is at lease one mol, preferably 1 to 5 mols, per mol of compound [II].

Compound [II] used as the starting material in the above-described reaction can be produced by a well-known method [J. Med. Chem., 7, 609 (1964)].

The halides represented by above general formula [III-II] can be produced from proline, hydroxyproline, and thioproline obtained by reacting cysteine with formaldehyde, by a known method [EPO 404359A1].

In method A-2, the stereochemical structures of the compounds of the present invention were determined according to a reaction mechanism described in literatures [[EPO 404359A1 and Tetrahedron, 37, 2173 (1981)].

Compounds [I-II] of the present invention can also be produced by following method B-2:

wherein $R^{11}$ through $R^{15}$, A, B, D and $Y^2$ are as defined above, V represents a group for protecting the amino group such as t-butoxycarbonyl group, benzyloxycarbonyl group or tosyl group, and W and W' each represent a leaving group such as chlorine atom, bromine atom, iodine atom, mesyl group or tosyl group.

Compounds [I-II] of the present invention can be produced by dropping, for example, an N-t-butoxycarbonyl-2-pyrrolidinylmethyl tosylate of above general formula [IV-II] into compound [II] to conduct the reaction in a solvent and thereby to form a compound of general formula [V-II], removing the protecting group to obtain a compound of general formula [VI-II] and reacting this compound with a compound of general formula [VII-II].

The reaction solvent used in this process may be the same as that used in above reaction method A-1.

Amino-substituted compounds can be produced by above-described method C.

The pharmacologically acceptable salts of compounds [I-I] and [I-II] of the present invention are mineral acid salts (inorganic acid salts) such as hydrochlorides, hydrobromides, sulfates and phosphates; and organic acid salts such as acetates, lactates, fumarates, maleates, malates, tartrates, citrates, oxalates, aspartates and methanesulfonates. Among them, the inorganic acid salts are preferred.

The compounds [I-I] and [I-II] of the present invention have one or more asymmetric carbon atoms and they can have optical isomers. The optical isomers, any mixtures of them and racemates are included in the compounds of the present invention. Among them, those wherein the configuration in 2-position of the pyrrolidine ring is in R-form are preferred. Since the compounds and pharmacologically acceptable salts thereof of the present invention can be in the form of their hydrates or solvated products, they are also included in the present invention.

When a compound of the present invention is used in the form of a pharmaceutical preparation or a pharmaceutical composition, it can be suitably mixed with pharmaceutical adjuvants such as a pharmaceutically acceptable excipient, carrier and diluent and orally or parenterally administered in the form of tablets, capsules, granules, fine granules, pills, syrup, suspension, emulsion, ointment, suppositories or injection prepared by an ordinary method. In the present invention, the medical preparation or medical composition comprising a compound of the present invention as the active ingredient and a pharmaceutically acceptable carrier and/or diluent is preferred. The carriers and diluents usable herein include glucose, sucrose, lactose, talc, silica, cellulose, methylcellulose, starch, gelatin, ethylene glycol, polyethylene glycol, glycerol, ethanol, water, oils and fats.

The dose and number of times of the administration of the compounds of the present invention can be suitably selected depending on the kind of the disease, and age and body weight of the patient. For example, in the oral administration of a compound of the present invention for treating intestinal diseases such as irritable bowel syndrome, the compound is given in an amount of about 0.1 to 1,000 mg/day all at once or in several portions a day.

The following Examples, Test Examples and Preparation Examples will further illustrate the present invention, which by no means limit t he invention so far as they are within the scope of the invention.

PREPARATION EXAMPLE 1

Preparation of (R)- and (S)-5,11-Dihydro-5-(2-pyrrolidinylmethyl)dibenzo[b,e][1,4]oxazepine 60% sodium hydride (1.44 g, 36 mmol) was washed with hexane under argon atmosphere, and then suspended in dimethyl sulfoxide (100 ml). 5,11-dihydrodibenzo[b,e][1,4]oxazepine [H. L. Yale, et al. J. Med. Chem., 7, 609 (1964)] (6.0 g, 30 mmol) was added to the obtained suspension, and the resultant mixture was stirred at 50° C. for 60 minutes. A solution of (R)-N-t-butoxycarbonyl-2-pyrrolidinylmethyl tosylate (12.8 g, 36 mmol) in dimethyl sulfoxide (60 ml) was dropped therein and the obtained mixture was stirred at 50° C. for 3 hours. The reaction solution was poured into 5% aqueous potassium bisulfate solution cooled with ice/water. After the extraction with ethyl acetate, the organic layer was washed with saturated aqueous sodium bicarbonate solution and then with saturated aqueous sodium chloride solution and dried. The solvent was evaporated under reduced pressure. The residue was treated by the column chromatography. After the elusion with a mixed solvent of ethyl acetate and hexane (1:11), the solvent was evaporated under reduced pressure to obtain (R)-5,11-dihydro-5-[1-(t-butoxycarbonyl)-2-pyrrolidinylmethyl]dibenzo[b,e][1,4] oxazepine (2.57 g, 22%).

4 M hydrochloride/dioxane solution (1.5 ml) was added to a solution of 400 mg of (R)-5,11-dihydro-5-[1-(t-butoxycarbonyl)-2-pyrrolidinylmethyl]dibenzo[b,e][1,4] oxazepine in dioxane (1.5 ml)), and the mixture was stirred at room temperature for one hour. The solvent was evaporated under reduced pressure. The residue was dissolved in dichloromethane (20 ml). Triethylamine (0.16 ml, 1.1 mmol) was added to the obtained solution, and the solution was stirred at room temperature for 30 minutes and then washed with saturated aqueous sodium bicarbonate solution. The organic layer was dried over magnesium sulfate. The solvent was evaporated under reduced pressure to obtain the title compound, i.e. (R)-5,11-dihydro-5-(2-pyrrolidinylmethyl)dibenzo [b,e][1,4]oxazepine, in the form of a light yellow oil(280 mg, 96%).

ESI/Mass: 281 [M+H+].

NMR(CDCl3) δ: 1.40–1.48(1H, m), 1.50–1.90(3H, m), 2.55(1H, b), 2.76–2.96(2H, m), 3.28–3.38(1H, m), 3.62–3.82(2H, m), 5.33(2H, s), 6.75–6.83 (3H, m), 6.97–7.03(2H, m), 7.10–7.15(1H, m), 7.24–7.32(2H, m).

(S)-5,11-dihydro-5-(2-pyrrolidinylmethyl)dibenzo[b,e][1,4] oxazepine was obtained from (S)-N-t-butoxycarbonyl-2-pyrrolidinylmethyl tosylate in the same manner as that described above. NMR and mass spectrum of this compound were the same as those described above.

EXAMPLE 1

(R)-5,11-Dihydro-5-[1-[2-(4-dimethylaminophenyl) ethyl]-2-pyrrolidinylmethyl]dibenzo [b,e][1,4] oxazepine (R)-5,11-dihydro-5-(2-pyrrolidinylmethyl)dibenzo[b,e] [1,4]oxazepine (Preparation Example 1) (420 mg, 1.5 mmol), 2-(4-dimethylaminophenyl)ethyl tosylate (640 mg, 2 mmol), sodium carbonate (210 mg, 2 mmol) and sodium iodide (30 mg, 0.2 mmol) were added to acetonitrile (20 ml), and the mixture was heated under reflux at 90° C. for 14 hours. The solvent was evaporated under reduced pressure, and the residue was partitioned in ethyl acetate and water. The organic layer was washed with water and then dried over magnesium sulfate. The solvent was evaporated under reduced pressure. The residue was treated by the column chromatography and then eluted with dichloromethane and then with dichloromethane/2 M methanolic ammonia (50:1) as the eluents. A suitable fraction was collected, and the solvent was evaporated under reduced pressure to obtain the title compound in the form of a light yellow oil (240 mg, 37%).

NMR(CDCl3) δ: 1.57–1.87(4H, m), 2.20–2.30(1H, m), 2.47–2.58(1H, m)2.73–2.79(3H, m), 2.94(6H, s), 2.99–3.10 (1H, m), 3.16–3.26(1H, m), 3.35 (1H, dd, J=9.4, 13.0 Hz), 4.10(1H, dd, J=3.6, 13.0 Hz), 5.21(1H, d, J=11.7 Hz), 5.33(1H, d, J=11.7 Hz), 6.72–6.85(3H, m), 6.86(2H,d,J=8.7 Hz) 6.92–7.08(3H, m), 7.14(2H, d, J=8.7 Hz), 7.20–7.35 (2H, m).

EXAMPLE 2

(R)-5,11-Dihydro-5-[1-[2-(4-dimethylaminophenyl) ethyl]-2-pyrrolidinylmethyl]dibenzo[b,e][1,4] oxazepine Dihydrochloride 0.6 ml of 4 M hydrochloride/dioxane was added to a solution of 238 mg of (R)-5,11-dihydro-5-[1-[2-(4-dimethylaminophenyl)ethyl]-2-pyrrolidinylmethyl]dibenzo [b,e][1,4]oxazepine in dichloromethane (10 ml), and the solution was stirred for 5 minutes. The solvent was evaporated under reduced pressure, and the residue was recrystallized from a mixed solvent of ethanol, dimethoxyethane and ether to obtain the title compound in the form of a white solid (204 mg, 73%).

Melting point: 164–169° C.; ESI/Mass: 428 [M+H+]; NMR(CDCl3) δ: 1.90–2.30(4H, m), 2.77–2.88(1H, m), 2.95–3.05(1H, m), 3.10–3.28(1H, m), 3.16(6H, s), 3.42–3.54(2H, m), 3.58–3.70(1H, m), 3.86–3.96(1H, m), 4.23(1H, dd, J=7.2, 14.1 Hz), 4.67(1H, dd, J=5.4, 14.1 Hz), 5.14(1H, d, J=12.6 Hz), 5.29(1H, d, J=12.6 Hz), 6.80–6.90 (3H, m), 7.00–7.14 (3H, m), 7.20–7.33(2H, m), 7.40(2H, d, 8.7 Hz), 7.74(2H, d, 8.7 Hz).

EXAMPLE 3

(S)-5,11-Dihydro-5-[1-[2-(4-dimethylaminophenyl) ethyl]-2-pyrrolidinylmethyl]dibenzo[b,e][1,4] oxazepine The title compound (yield: 38%) was obtained from (S)-5,11-dihydro-5-(2-pyrrolidinylmethyl)dibenzo[b,e][1,4] oxazepine (Preparation Example 1) in the same manner as that of Example 1. This compound had the same NMR and mass spectrum as those of the compound obtained in Example 1.

EXAMPLE 4

(S)-5,11-Dihydro-5-[1-[2-(4-dimethylaminophenyl) ethyl]-2-pyrrolidinylmethyl]dibenzo[b,e][1,4] oxazepine Dihydrochloride The title compound was obtained in the form of a white solid (yield: 72%) by treating the compound obtained in Example 3 in the same manner as that of Example 2. The product had the same NMR and mass spectrum as those of the compound obtained in Example 2.

Melting point: 165–170° C.

EXAMPLE 5

(R)-5,11-Dihydro-5-[1-[2-(4-diethylaminophenyl) ethyl]-2-pyrrolidinylmethyl]dibenzo[b,e][1,4] oxazepine The title compound was obtained in the form of a light yellow oil (yield: 74%) by using 2-(4-diethylaminophenyl) ethyl bromide in the same manner as that of Example 1.

NMR(CDCl3) δ: 1.16(6H, t, J=8.0 Hz), 1.63–1.90(4H, m), 2.25–2.35(1H, m), 2.50–2.62(1H, m), 2.70–2.86(3H, m), 3.03–3.15(1H, m), 3.22–3.30(1H, m), 3.36(4H, q, J=8.0 Hz), 3.41(1H, dd, J=10.7, 14.3 Hz), 4.17(1H, dd, J=3.7, 14.3 Hz), 5.26(1H, d, J=13.0 Hz), 5.34(1H, d, J=13.0 Hz), 6.65(2H, d, J=11.7 Hz), 6.76–6.82(3H, m), 6.99–7.12(3H, m), 7.07(2H, d, 11.7 Hz), 7.25–7.32(2H, m).

EXAMPLE 6

(R)-5,11-Dihydro-5-[1-[2-(4-diethylaminophenyl) ethyl]-2-pyrrolidinylmethyl]dibenzo[b,e][1,4] oxazepine Dihydrochloride The title compound was obtained in the form of a white solid (yield: 90%) by treating the compound obtained in Example 5 in the same manner as that of Example 2.

Melting point: 143–146° C.; ESI/Mass: 456 [M+H+]; NMR(CD3OD) δ: 1.15(6H, t, J=8.0 Hz), 1.92–2.26(3H, m), 2.33–2.47(1H, m), 3.03–3.17(2H, m), 3.22–3.35(2H, m), 3.53–3.60(1H, m), 3.60–3.70(4H, m), 3.70–3.80(1H, m), 4.04(1H, dd, J=10.3, 14.6 Hz), 4.33(1H, dd, J=5.0, 14.6 Hz), 5.18(1H, d, J=14.0 Hz), 5.50(1H, d, J=14.0 Hz), 6.80–6.94 (3H, m), 7.10 –7.20(2H, m), 7.23–7.30(2H, m), 7.35–7.57 (5H, m).

EXAMPLE 7

(R)-5,11-Dihydro-5-[1-[2-(4-aminophenyl)ethyl]-2-pyrrolidinylmethyl]dibenzo[b,e][1,4]oxazepine Dihydrochloride (R)-5,11-dihydro-5-(2-pyrrolidinylmethyl)dibenzo[b,e] [1,4]oxazepine (Preparation Example 1) (220 mg, 0.78 mmol), 2-[4-(N-t-butoxycarbonylamino)phenyl]ethyl chloride (400 mg, 1.02 mmol), sodium carbonate (110 mg, 1.02 mmol) and sodium iodide (20 mg, 0.13 mmol) were added to acetonitrile (15 ml), and the mixture was heated under reflux at 90° C. for 15 hours. The solvent was evaporated under reduced pressure, and the residue was partitioned in ethyl acetate and water. The organic layer was washed with water and then dried over magnesium sulfate. The solvent was evaporated under reduced pressure. The residue was treated by the column chromatography and then eluted with dichloromethane as the eluent. A suitable fraction was collected, and the solvent was evaporated under reduced pressure to obtain (R)-5,11-dihydro-5-[1-[2-(4-N-t-butoxycarbonylamino)phenyl)ethyl]-2-pyrrolidinylmethyl] dibenzo[b,e][1,4]oxazepine in the form of a light yellow oil (380 mg, 97%).

NMR(CDCl3) δ: 1.51(9H, s), 1.62–1.90(4H, m), 2.20–2.32(1H, m), 2.48–2.56(1H, m), 2.72–2.80(3H, m), 3.00–3.10(1H, m), 3.16–3.22(1H, m), 3.35(1H, dd, J=10.7, 14.3 Hz), 4.08(1H, dd, J=3.7, 14.3 Hz), 5.21(1H, d, J=13.0 Hz), 5.32(1H, d, J=13.0 Hz), 6.74–6.86(3H, m), 6.96–7.08 (3H, m), 7.13 (2H, d, J=9.3 Hz), 7.25–7.35(2H, m), 7.29(2H, d, 9.3 Hz).

This product was treated in the same manner as that of Example 2 to obtain the title compound in the form of a white solid (yield: 57%). Melting point: 176–180° C.; ESI/ Mass: 400[M+H+]; NMR(CD3OD) δ: 1.92–2.20(3H, m), 2.32–2.45(1H, m), 3.00–3.14(2H, m), 3.20–3.34(2H, m), 3.48–3.58(1H, m), 3.72–3.80(1H, m), 3.84–3.96(1H, m), 4.37(1H, dd, J=4.7, 15.3 Hz), 4.02(1H, dd, J=10.7, 11513z), 5.19(1H, d, J=14.3 Hz), 5.50(1H, d, J=14.3 Hz), 6.83–6.96 (3H, m), 7.09–7.20(3H, m), 7.25 –7.40(6H, m).

EXAMPLE 8

(R)-5,11-Dihydro-5-[1-[2-(4-methylaminophenyl) ethyl]-2-pyrrolidinylmethyl]dibenzo[b,e][1,4] oxazepine Dihydrochloride (R)-5,11-Dihydro-5-[1-[2-(4-N-t-butoxycarbonyl-N-methylaminophenyl)ethyl]-2-pyrrolidinylmethyl]dibenzo[b, e][1,4]oxazepine was obtained by using 2-[4-(N-t-butoxycarbonyl-N-methylamino)phenyl]ethyl chloride in the form of a light yellow oil (yield: 82%) in the same manner as that of Example 7.

NMR(CDCl3) δ: 1.46(9H, s), 1.64–1.90(4H, m), 2.22–2.30(1H, m), 2.52 –2.60(1H, m), 2.74–2.84(3H, m), 3.03–3.13(1H, m), 3.16–3.25(1H, m), 3.16(3H, s), 3.35(1H, dd, J=10.7, 14.3 Hz), 4.09(1H, dd, J=3.7, 14.3 Hz), 5.21(1H, d, J=13.0 Hz), 5.32(1H, d, J=13.0 Hz), 6.75–6.86(3H, m), 7.00–7.20 (7H, m), 7.28–7.34(2H, m).

This product was treated in the same manner as that of Example 2 to obtain the title compound in the form of a white solid (yield: 63%).

Melting point: 134–137° C.; ESI/Mass: 414[M+H+];

NMR(CD3OD) δ: 1.94–2.20(3H, m), 2.32–2.46(1H, m), 3.00–3.15(2H, m), 3.06(3H, s), 3.20–3.38(2H, m), 3.50–3.60(1H, m), 3.72–3.80(1H, m), 3.84–3.95(1H, m), 4.04(1H, dd, J=10.3, 15.7 Hz), 4.32(1H, dd, J=5.3, 15.7 Hz), 5.19(1H, d, J=14.0 Hz), 5.50(1H, d, J=14.0 Hz), 6.82–6.96 (3H, m), 7.10–7.20 (2H, m), 7.27–7.35(2H, m), 7.37–7.50 (5H, m).

EXAMPLE 9

(R)-5,11-Dihydro-5-[1-[2-(3-dimethylaminophenyl) ethyl]-2-pyrrolidinylmethyl]dibenzo[b,e][1,4] oxazepine The title compound was obtained in the form of a light yellow oil (yield: 56%) by using 2-(3-dimethylaminophenyl)ethyl tosylate in the same manner as that of Example 1.

NMR(CDCl3) δ: 1.63–1.90(4H, m), 2.21–2.31(1H, m), 2.54–2.63(1H, m), 2.73–2.82(3H, m), 2.95(6H, s), 3.06–3.14(1H, m), 3.17–3.26(1H, m), 3.37(1H, dd, J=10.7, 14.3 Hz), 4.12(1H, dd, J=3.7, 14.3 Hz), 5.22(1H, d, J=13.0 Hz), 5.34(1H, d, J=13.0 Hz), 6.58–6.63(3H, m), 6.76–6.83 (3H, m), 6.98–7.32(6H, m).

EXAMPLE 10

(R)-5,11-Dihydro-5-[1-[2-(3-dimethylaminophenyl) ethyl]-2-pyrrolidinylmethyl]dibenzo[b,e][1,4] oxazepine Dihydrochloride The title compound was obtained in the form of a white solid (yield: 89%) by treating the compound obtained in Example 9 in the same manner as that of Example 2.

Melting point: 125–128° C.; ESI/Mass : 428 [M+H+]; NMR(CD3OD) δ: 1.95–2.20(3H, m), 2.33–2.43(1H, m), 3.02–3.15(2H, m), 3.20–3.36(2H, m), 3.28(6H, s), 3.54–3.64(1H, m), 3.72–3.80(1H, m), 3.83–3.92(1H, m), 4.08(1H, dd, J=10.0, 15.7 Hz), 4.30(1H, dd, J=5.7, 15.7 Hz), 5.20(1H, d, J=14.3 Hz), 5.52(1H, d, J=14.3 Hz), 6.80–6.95 (3H, m), 7.08–7.20 (2H, m), 7.24–7.40(4H, m), 7.7.48–7.57 (3H, m).

EXAMPLE 11

(S)-5,11-Dihydro-5-[1-[2-(3-dimethylaminophenyl) ethyl]-2-pyrrolidinylmethyl]dibenzo[b,e][1,4] oxazepine The title compound (yield: 62%) was obtained from (S)-5,11-dihydro-5-(2-pyrrolidinylmethyl)dibenzo[b,e][1,4] oxazepine (Preparation Example 1) in the same manner as that of Example 9. This compound had the same NMR and mass spectrum as those of the compound obtained in Example 9.

EXAMPLE 12

(S)-5,11-Dihydro-5-[1-[2-(4-dimethylaminophenyl) ethyl]-2-pyrrolidinylmethyl]dibenzo[b,e][1,4] oxazepine Dihydrochloride The title compound was obtained in the form of a light brown solid (yield: 79%) by treating the compound obtained in Example 11 in the same manner as that of Example 2. The product had the same NMR and mass spectrum as those of the compound obtained in Example 10.

EXAMPLE 13

(R)-5,11-Dihydro-5-[1-[2-(3-aminophenyl)ethyl]-2-pyrrolidinylmethyl]dibenzo[b,e][1,4]oxazepine Dihydrochloride (R)-5,11-Dihydro-5-[1-[2-(3-(N-t-butoxycarbonyl) aminophenyl)ethyl]-2-pyrrolidinylmethyl]dibenzo[b,e][1,4] oxazepine was obtained in the form of a light yellow oil (yield: 90%) by using 2-[3-(N-t-butoxycarbonylamino) phenyl]ethyl chloride in the same manner as that of Example 7.

NMR(CDCl3) δ: 1.52(9H, s), 1.65–1.90(4H, m), 2.20–2.28(1H, m), 2.52–2.60(1H, m), 2.73–2.84(3H, m), 3.03–3.14(1H, m), 3.15–3.21(1H, m), 3.37(1H, dd, J=10.7, 14.3 Hz), 4.09(1H, dd, J=3.7, 14.3 Hz), 5.21(1H, d, J=13.3 Hz), 5.33(1H, d, J=13.3 Hz), 6.75–6.90(4H, m), 7.00–7.15 (3H, m), 7.16 –7.36(5H, m).

This product was treated in the same manner as that of Example 2 to obtain the title compound in the form of a white solid (84%).

Melting point: 149–152° C.; ESI/Mass: 400 [M+H+] NMR(CD3OD) δ: 1.93–2.20(3H, m), 2.32–2.46(1H, m), 3.03–3.20(1H, m), 3.24–3.36(1H, m), 3.52–3.64(1H, m), 3.70–3.80(1H, m), 3.82–3.96(1H, m), 4.07(1H, dd, J=10.0, 15.3 Hz), 4.30(1H, dd, J=5.7, 15.3 Hz), 5.21(1H, d, J=14.0 Hz), 5.48(1H, d, J=14.0 Hz), 6.83–6.96(3H, m), 7.08–7.20 (2H, m), 7.25 –7.55(7H, m)

EXAMPLE 14

(R)-5,11-Dihydro-5-[1-[2-(3-methylaminophenyl) ethyl]-2-pyrrolidinylmethyl]dibenzo[b,e][1,4] oxazepine Dihydrochloride (R)-5,11-Dihydro-5-[1-[2-(3-(N-t-butoxycarbonyl-N-methyl)aminophenyl)ethyl]-2-pyrrolidinylmethyl]dibenzo [b,e][1,4]oxazepine was obtained in the form of a light yellow oil (yield: 83%) by using 2-[3-(N-t-butoxycarbonyl-N-methylamino)phenyl]ethyl tosylate in the same manner as that of Example 7.

NMR(CDCl3) δ: 1.47(9H, s), 1.64–1.90(4H, m), 2.20–2.30(1H, m), 2.74–2.86(3H, m), 3.03–3.14(1H, m), 3.15–3.24(1H, m), 3.27(3H, s), 3.37(1H, dd, J=10.7, 14.3 Hz), 4.10(1H, dd, J=3.7, 14.3 Hz), 5.22(1H, d, J=13.3 Hz), 5.34(1H, d, J=13.0 Hz), 6.67–6.83(3H, m), 7.99–7.05(3H, m), 7.09–7.12(3H, m), 7.23–7.30(3H, m).

This product was treated in the same manner as that of Example 2 to obtain the title compound in the form of a white solid (63%).

Melting point: 179–181° C.; ESI/Mass: 414[M+H+]; NMR(CD3OD) δ: 1.95–2.20(3H, m), 2.32–2.43(1H, m), 30.4–3.10(2H, m), 3.08(3H, s), 3.56–3.66(1H, m), 3.70–3.80(1H, m), 3.83–3.95(1H, m), 4.08 (1H, dd, J=10.0, 16.0 Hz), 4.30(1H, dd, J=5.7, 16.0 Hz), 5.21(1H, d, J=14.0 Hz), 5.50(1H, d, J=14.0 Hz), 6.80–6.95(3H, m), 7.12–7.20 (2H, m), 7.25–7.40 (6H, m), 7.48–7.54(1H, m).

EXAMPLE 15

(S)-5,11-Dihydro-5-[1-[2-(3-methylaminophenyl) ethyl]-2-pyrrolidinylmethyl]dibenzo[b,e][1,4] oxazepine Dihydrochloride (S)-5,11-Dihydro-5-[1-[2-(3-(N-t-butoxycarbonyl-N-methyl)aminophenyl)ethyl]-2-pyrrolidinylmethyl]dibenzo [b,e][1,4]oxazepine was obtained in the form of a light yellow oil (yield: 58%) by using (S)-5,11-dihydro-5-(2-pyrrolidinylmethyl)dibenzo[b,e][1,4]oxazepine (Preparation Example 1) in the same manner as that of Example 14.

The title compound was obtained in the form of a light brown solid (yield: 80%) by treating the compound, obtained as described above, in the same manner as that of Example 2 and then evaporating the solvent under reduced pressure. The product had the same NMR and mass spectrum as those of the compound obtained in Example 14.

EXAMPLE 16

(R)-5,11-Dihydro-5-[1-[2-(2-aminophenyl)ethyl]-2-pyrrolidinylmethyl]dibenzo[b,e][1,4]oxazepine (R)-5,11-dihydro-5-[1-[2-(2-(N-t-butoxycarbonylamino) phenyl)ethyl]-2-pyrrolidinylmethyl]dibenzo[b,e][1,4] oxazepine was obtained from 2-[2-(N-t-butoxycarbonylamino)phenyl]ethyl tosylate in the same manner as that of Example 7. This product was dissolved in dichloromethane. 4 M hydrochloride/dioxane was added to the obtained solution, and the mixture was stirred at room temperature for one hour. The solvent was evaporated. The residue was partitioned in 0.5 M-NaOH and chloroform. The organic layer was dried over magnesium sulfate. The solvent was evaporated under reduced pressure to obtain the title compound in the form of a light yellow oil (yield: 43%).

NMR(CDCl3) δ: 1.60–1.90(4H, m), 2.20–2.28(1H, m), 2.56–2.65(1H, m), 2.70–2.81(3H, m), 3.02–3.11(1H, m), 3.22–3.27(1H, m), 3.33(1H, dd, J=10.7, 14.1 Hz), 4.07(1H, dd, J=4.3, 14.1 Hz), 5.17(1H, d, J=13.0 Hz), 5.29(1H, d, J=13.0 Hz), 6.65–6.80(5H, m), 6.92–7.08(5H, m), 7.20–7.34 (2H, m).

EXAMPLE 17

(R)-5,11-Dihydro-5-[1-[2-(2-aminophenyl)ethyl]-2-pyrrolidinylmethyl]dibenzo[b,e][1,4]oxazepine Dihydrochloride The compound obtained in Example 16 was treated in the same manner as that of Example 2 to obtain the title compound in the form of a white solid (yield: 88%).

Melting point: 168–172° C.; ESI/Mass: 400 [M+H+];

NMR(CD3OD) δ: 1.96–2.20(3H, m), 2.32–2.41(1H, m), 3.14–3.20(2H, m), 3.30–3.44(2H, m), 3.70–3.83(2H, m), 3.84–3.94(1H, m), 4.24(1H, s), 4.26 (1H, s), 5.18(1H, d, J=14.0 Hz), 5.43(1H, d, J=14.0 Hz), 6.83–6.95(3H, m), 7.10–7.20(2H, m), 7.25–7.44(7H, m).

EXAMPLE 18

(R)-5,11-Dihydro-5-[1-[2-(2-dimethylaminophenyl) ethyl]-2-pyrrolidinylmethyl)dibenzo[b,e][1,4] oxazepine The compound (130 mg, 0.32 mmol) obtained in Example 16 was dissolved in 3 ml of acetonitrile. 37% aqueous formaldehyde solution (0.3 ml, 3.7 mmol) and sodium cyanoborohydride (30 mg, 0.48 mmol) were added to the obtained solution and thereby dissolved therein. 0.2 ml of glacial acetic acid was added dropwise under vigorous stirring and the mixture was stirred at room temperature for 0.5 hour. The reaction mixture was neutralized with solid sodium bicarbonate. After the extraction with ethyl acetate, the organic layer was washed with magnesium sulfate. The solvent was evaporated under reduced pressure. The residue was treated by the column chromatography. After the elusion with dichloromethane and then with dichloromethane/ methanol (50:1), a suitable fraction was taken. The solvent was evaporated under reduced pressure to obtain the title compound in the form of a light yellow oil (95 mg, 69%).

NMR(CDCl3) δ: 1.64–1.90(4H, m), 2.25–2.35(1H, m), 2.57–2.66(1H, m), 2.69(6H, s), 2.74–2.87(1H, m), 2.90–3.00(2H, m), 3.08–3.17(1H, m), 3.23–3.29(1H, m), 3.39(1H, dd, J=10.7, 14.0 Hz), 4.15(1H, dd, J=4.0, 14.0 Hz), 5.21(1H, d, J=14.0 Hz), 5.32(1H, d, J=14.0 Hz), 6.74–6.83 (3H, m), 7.00–7.08 (3H, m), 7.12–7.17(2H, m), 7.20–7.23 (2H, m), 7.28–7.34(2H, m).

EXAMPLE 19

(R)-5,11-Dihydro-5-[1-[2-(3-dimethylaminophenyl) ethyl]2-pyrrolidinylmethyl)dibenzo[b,e][1,4] oxazepine Dihydrochloride The compound obtained in Example 18 was treated in the same manner as that of Example 2 to obtain the title compound in the form of a white solid (56%).

Melting point: 170–172° C.; ESI/Mass: 428[M+H+]; NMR(CD3OD) δ: 1.93–2.18(3H, m), 2.32–2.47(1H, m), 3.17(6H, s), 3.25 –3.33(2H, m), 3.34–3.44(2H, m), 3.68–3.88(2H, m), 3.90–3.97(1H, m), 4.25(1H, s), 4.27(1H, s), 5.08(1H, d, J=14.7 Hz), 5.35(1H, d, J=14.7 Hz), 6.75–6.95(3H, m), 7.06–7.20(2H, m), 7.25–7.80(7H, m)

EXAMPLE 20

(R)-5,11-Dihydro-5-[1-[2-(3-dimethylamino-4-methoxyphenyl)ethyl]-2-pyrrolidinylmethyl]dibenzo [b,e][1,4]oxazepine The title compound was obtained in the form of a light yellow oil (yield: 64%) by using 2-(3-dimethylamino-4-methoxyphenyl)ethyl tosylate in the same manner as that of Example 1.

NMR(CDCl3) δ: 1.63–1.90(4H, m), 2.20–2.36(1H, m), 2.50–2.64(1H, m), 2.70–2.86(3H, m), 2.79(6H, s), 3.00–3.16(1H, m), 3.18–3.24(1H, m), 3.38·(1H, t, J=13.0 Hx), 3.97(3H, s), 4.10(1H, d , J=13.0 Hz), 5.21(1H, d, J=14.0 Hz), 5.34(1H, d, J=14.0 Hz), 6.76–6.86(6H, m), 7.00–7.16(3H, m), 7.24–7.32(2H, m).

EXAMPLE 21

(R)-5,11-Dihydro-5-[1-[2-(3-dimethylamino-4-methoxyphenyl)ethyl]-2-pyrrolidinylmethyl]dibenzo [b,e][1,4]oxazepine Dihydrochloride The title compound was obtained in the form of a white solid (yield: 72%) by treating the compound obtained in Example 20 in the same manner as that of Example 2.

Melting point: 141–144° C.; ESI/Mass: 458[M+H+]; NMR(CD3OD) δ: 1.94–2.20(3H, m), 2.32–2.42(1H, m), 3.00–3.16(2H, m), 3.23–3.36(2H, m), 3.27(6H, s), 3.50–3.63(1H, m), 3.70–3.80(1H, m), 3.82–3.92(1H, m), 4.04(3H, s), 4.08(1H, dd, J=10.3, 15.7 Hz), 4.30(1H, dd, J=5.3, 15.7 Hz), 5.21(1H, d, J=14.0 Hz), 5.54(1H, d, J=14.0 Hz), 6.80–6.94(3H, m), 7.10–7.20(2H, m), 7.25–7.40(5H, m), 7.70(1H, s).

EXAMPLE 22

(R)-5,11-Dihydro-5-[1-[2-(4-methoxyy-3-aminophenyl)ethyl]-2-pyrrolidinylmethyl]dibenzo[b,e][1,4]oxazepine Dihydrochloride (R)-5,11-Dihydro-5-[1-[2-[3-(N-t-butoxycarbonylamino)-4-methoxyphenyl]ethyl]-2-pyrrolidinylmethyl]dibenzo[b,e][1,4]oxazepine was obtained in the form of a light yellow oil (yield: 86%) by using 2-[3-(N-t-butoxycarbonylamino)-4-methoxy]phenylethyl tosylate in the same manner as that of Example 7.

NMR(CDCl3) δ: 1.52(9H, s), 1.63–1.90(4H, m), 2.20–2.30(1H, m), 2.50 –2.62(1H, m), 2.72–2.80(3H, m), 3.04–3.17(1H, m), 3.18–3.24(1H, m), 3.30–3.40(1H, m), 3.85(3H, s), 4.12–4.18(1H, m), 5.20(1H, d, J=14.0 Hz), 5.34(1H, d, J=14.0 Hz), 6.74–6.84(5H, m), 7.00–7.08(2H, m), 7.10–7.16(2H, m), 7.23–7.36(2H, m).

This product was treated in the same manner as that of Example 2 to obtain the title compound in the form of a white solid (69%).

Melting point: 151–155° C.; ESI/Mass: 430 [M+H+];
NMR(CD3OD) δ: 1.92–2.20(3H, m), 2.30–2.42(1H, m), 2.92–3.08(2H, m), 3.18–3.30(2H, m), 3.48–3.56(1H, m), 3.68–3.78(1H, m), 3.83–3.93(1H, m), 3.97(3H, s), 4.06(1H, dd, J=10.0, 15.7 Hz), 4.29(1H, dd, J=5.7, 15.7 Hz), 5.21(1H, d, J=14.0 Hz), 5.49(1H, d, J=14.0 Hz), 6.82–6.94(3H, m), 7.08–7.18 (3H, m), 7.26–7.40(5H, m).

EXAMPLE 23

(R)-5,11-Dihydro-5-[1-[3-(4-methoxyphenyl)propane-1-yl]-2-pyrrolidinylmethyl]dibenzo[b,e][1,4]oxazepine (R)-5,11-dihydro-5-(2-pyrrolidinylmethyl)dibenzo [b,e][1,4]oxazepine (Preparation Example 1) (280 mg, 1.0 mmol), 3-(4-methoxyphenyl)-1-propyl bromide (320 mg, 1.4 mmol), sodium carbonate (150 mg, 1.4 mmol) and sodium iodide (20 mg, 0.13 mmol) were added to acetonitrile (20 ml), and the mixture was heated under reflux at 90° C. for 13 hours. The solvent was evaporated under reduced pressure, and the residue was partitioned in ethyl acetate and water. The organic layer was washed with water and then dried over magnesium sulfate. The solvent was evaporated under reduced pressure. The residue was treated by the column chromatography and then eluted with dichloromethane as the eluent. A suitable fraction was collected, and the solvent was evaporated under reduced pressure to obtain the title compound in the form of a light yellow oil (310 mg, 72%).

NMR(CDCl3) δ: 1.60–1.90(6H, m), 2.10–2.20(1H, m), 2.28–2.38(1H, m)·2.53–2.77 (4H, m), 2.80–2.90(1H, m), 3.12–3.18(1H, m), 3.40(1H, dd, J=9.4, 13.0 Hz), 3.80(3H, s), 4.08(1H, dd, J=3.6, 13.0 Hz), 5.22(1H, d, J=11.7 Hz), 5.33(1H, d, J=11.7 Hz), 6.76–6.90(3H, m), 6.86(2H, d, J=8.7 Hz)·6.94–7.10(3H, m), 7.16(2H, d, J=8.7 Hz), 7.28–7.35 (2H, m).

EXAMPLE 24

(R)-5,11-Dihydro-5-[1-[3-(4-methoxyphenyl)propane-1-yl]-2-pyrrolidinylmethyl]dibenzo[b,e][1,4]oxazepine Hydrochloride 0.5 ml of 4 M hydrochloride/dioxane was added to a solution of 290 mg of the compound obtained in Example 23 in dichloromethane (10 ml), and the mixture was stirred for 5 minutes. The solvent was evaporated under reduced pressure. The residue was recrystallized from a mixed solvent of acetone and ether to obtain the title compound in the form of a white solid (268 mg, 79%).

Melting point: 172–174° C.; ESI/Mass: 429 [M+H+];
NMR(CDCl3) δ: 1.86–2.08(2H, m), 2.12–2.28(3H, m), 2.30–2.46(1H, m)2.57–2.80(4H, m), 3.25–3.36(2H, m), 3.78 (3H, s), 3.80–3.88(1H, m), 4.20 (1H, dd, J=7.2, 14.1 Hz), 4.58(1H, dd, J=5.1, 14.1 Hz), 5.16(1H, d, J=12.3 Hz), 5.25(1H, d, J=12.3 Hz), 6.77–6.91(3H, m), 6.80(2H, d, J=8.7), 6.95–7.10(3H, m), 7.04(2H, d, J=8.7), 7.21–7.33 (2H, m).

EXAMPLE 25

5,11-Dihydro-5-[[(2R)-1-[(3S)-3-hydroxy-3-phenylpropane-1-yl]-2-pyrrolidinyl]methyl]dibenzo[b,e][1,4]oxazepine.

The title compound was obtained in the form of a light yellow oil (yield: 78%) by using (S)-(+)-3-chloro-1-phenyl-1-propanol in the same manner as that of Example 23.

ESI/Mass: 415 [M+H+]; NMR(CDCl3) δ: 1.57–1.96(6H, m), 2.05–2.15(1H, m), 2.57–2.66(1H, m)·2.70–2.80 (1H, m), 3.08–3.30(1H, m), 3.30–3.40(1H, m), 3.42(1H, dd, J=9.9, 12.9 Hz), 4.26(1H, dd, J=3.0, 12.9 Hz), 4.93–5.00 (1H, m), 5.25(1H, d, J=11.7 Hz), 5.32(1H, d, J=11.7 Hz), 6.76–6.90(3H, m), 6.98–7.08(2H, m), 7.12–7.18(1H, m), 7.20–7.40(7H, m).

EXAMPLE 26

5,11-Dihydro-5-[[(2R)-1-[(3S)-3-hydroxy-3-phenylpropane-1-yl]-2-pyrrolidinyl]methyl]dibenzo[b,e][1,4]oxazepine Hydrochloride The title compound was obtained in the form of a white solid (yield: 55%) by treating the compound obtained in Example 25 in the same manner as that of Example 24.

Melting point: 149–150° C. ESI/Mass: 415 [M+H+];
NMR(CDCl3) δ: 1.90–2.00(1H, m), 2.02–2.28(3H, m), 2.30–2.41(1H, m)2.70–2.82(1H, m), 2.85–3.00(1H, m), 3.36–3.48(1H, m), 3.64–3.76(2H, m), 3.86–3.96(1H, m), 4.21(1H, dd, J=8.4, 14.1 Hz), 4.71(1H, dd, J=4.5, 14.1 Hz), 5.03–5.06(1H, m), 5.23(1H, d, J=12.0 Hz), 5.28(1H, d, J=12.0 Hz), 6.80–6.88(3H, m), 7.03–7.17(3H, m), 7.25–7.38 (7H, m).

EXAMPLE 27

5,11-Dihydro-5-[[(2R)-1-[(3S)-3-hydroxy-3-phenylpropane-1-yl]-2-pyrrolidinyl]methyl]dibenzo[b,e][1,4]oxazepine The title compound was obtained in the form of a light yellow oil (yield: 78%) by using (R)-(−)-3-chloro-1-phenyl-1-propanol in the same manner as that of Example 23.

NMR(CDCl3) δ: 1.60–1.95(5H, m), 2.15–2.25(2H, m), 2.45–2.53(1H, m)·2.60–2.70 (1H, m), 2.92–3.00(1H, m), 3.30–3.38(1H, m), 3.31(1H, dd, J=9.9, 12.9 Hz), 4.05(1H, dd, J=3.0, 12.9 Hz), 5.05–5.09(1H, m), 5.19(1H, d, J=11.7 Hz), 5.28(1H, d, J=11.7 Hz), 6.72–6.80(3H, m), 6.86–6.94 (1H, m), 6.96–7.02(2H; m), 7.22–7.32(3H, m), 7.37–7.44 (2H, m), 7.48–7.54(2H,m).

EXAMPLE 28

5,11-Dihydro-5-[[(2R)-1-[(3R)-3-hydroxy-3-phenylpropane-1-yl]-2-pyrrolidinyl]methyl]dibenzo[b,e][1,4]oxazepine Hydrochloride The title compound was obtained in the form of a white solid (yield: 74%) by treating the compound obtained in Example 27 in the same manner as that of Example 24.

Melting point: 179–182° C.; ESI/Mass: 415 [M+H+]; NMR(CDCl3) δ: 1.90–2.00(1H, m), 2.02–2.26(3H, m), 2.28–2.41(1H, m)2.75–2.88(1H, m), 2.97–3.07(1H, m), 3.36–3.48(1H, m), 3.50–3.78(2H, m), 3.92–4.03(1H, m), 4.17(1H, dd, J=8.7, 14.1 Hz), 4.67(1H, dd, J=4.5, 14.1 Hz), 4.88–4.92(1H, m), 5.19(1H, d, J=12.3 Hz), 5.26(1H, d, J=12.3 Hz), 6.80–6.92(3H, m), 6.98–7.15(3H, m), 7.20–7.38 (7H, m).

EXAMPLE 29

5,11-Dihydro-5-[[(2R)-1-[(2R)-2-hydroxy-3-(4-methoxyphenyl)propane-1-yl]-2-pyrrolidinyl]methyl]dibenzo[b,e][1,4]oxazepine The title compound was obtained in the form of a light yellow oil (yield: 78%) by using (R)-(-)-3-chloro-1-(4-methoxyphenyl)-2-propanol [C. F. Koelsch et al., J. Am. Chem. Soc., 52, 1164 (1930)] in the same manner as that of Example 23.

NMR(CDCl3) δ: 1.62–1.88(4H, m), 2.23–2.31(2H, m), 2.70–2.78(3H, m)2.82–2.92 (1H, m), 3.05–3.15(1H, m), 3.32(1H, dd, J=9.9, 12.9 Hz), 3.80·(3H, s), 3.83–3.94(1H, m), 4.05(1H, dd, J=3.6, 12.9 Hz), 5.21(1H, d, J=12.0 Hz), 5.30(1H, d, J=12.0 Hz), 6.76–6.80(3H, m), 6.86(2H,d,J=8.7 Hz) 6.94 –7.10(3H, m), 7.16(2H, d, J=8.7 Hz), 7.28–7.35 (2H, m).

EXAMPLE 30

The title compound was obtained in the form of a white solid (yield: 74%) by treating the compound obtained in Example 29 in the same manner as that of Example 24.

Melting point: 178–181° C. ESI/Mass: 445 [M+H+]; NMR(CDCl3) δ: 1.88–2.00(1H, m), 2.00–2.26(3H, m), 2.62–2.68(1H, m)2.82–2.97(3H, m), 3.18–3.35(1H, m), 3.77 (3H, s), 3.98–4.08(1H, m), 4.13 (1H, dd, J=8.4, 13.8 Hz), 4.28(1H, d, J=5.1), 4.52(1H, dd, J=4.6, 13.8 Hz), 4.53–4.62 (1H, m), 5.16(1H, d, J=12.6 Hz), 5.24(1H, d, J=12.6 Hz), 6.79–6.91 (4H, m), 6.83(2H, d, J=8.7), 6.98–7.11(2H, m), 7.08(2H, d, J=8.7), 7.19–7.30(2H, m).

EXAMPLE 31

(R)-5,11-Dihydro-5-[1-[3-(4-methoxyphenyl)-2-propene-1-yl]-2-pyrrolidinylmethyl]dibenzo [b,e][1,4]oxazepine The title compound was obtained in the form of a light yellow oil (yield: 29%) by using 4-methoxycinnamyl bromide in the same manner as that of Example 23.

NMR(CDCl3) δ: 1.68–1.92(4H, m), 2.37–2.44(1H, m), 2.92–3.00(1H, m)·3.16–3.24 (1H, m), 3.30–3.50(2H, m), 3.55(1H, dd, J=9.4, 13.0 Hz), 3.80·(3H, s), 4.19(1H, dd, J=3.6, 13.0 Hz), 5.23(1H, d, J=11.7 Hz), 5.34(1H, d, J=11.7 Hz), 6.20–6.32(1H, m), 6.50(d, J=16.0 Hz), 6.70–6.80(3H, m), 6.86 (2H,d,J=8.7 Hz) 6.96–7.12(3H, m), 7.17–7.28(2H, m), 7.32(2H, d, J=8.7 Hz).

EXAMPLE 32

(R)-5,11-Dihydro-5-[1-[3-(4-methoxyphenyl)-2-propene-1-yl]-2-pyrrolidinylmethyl]dibenzo[b,e][1,4]oxazepine Hydrochloride The title compound was obtained in the form of a white solid (yield: 46%) by treating the compound obtained in Example 31 in the same manner as that of Example 24.

Melting point: 120–122° C.; ESI/Mass: 427 [M+H+]; NMR(CDCl3) δ: 1.88–2.00(1H, m), 2.10–2.20(3H, m), 2.85–2.95(1H, m)3.55–3.68(1H, m), 3.70–3.92(3H, m), 3.80 (3H, s), 4.13(1H, dd, J=9.0, 13.8 Hz), 4.61(1H, dd, J=5.1, 13.8 Hz), 5.19(1H, d, J=12.3 Hz), 5.34(1H, d, J=12.3 Hz), 6.25–6.35(1H, m), 6.53(1H, d, J=15.9), 6.67–6.85(3H, m), 6.87·(2H, d, J=8.7), 6.93–7.08(3H, m), 7.14–7.22(7H, m), 7.34(2H, d, J=8.7).

EXAMPLE 33

(R)-5,11-Dihydro-5-[1-[2-(4-methoxyphenyloxy)ethyl]-2-pyrrolidinylmethyl]dibenzo [b,e][1,4]oxazepine The title compound was obtained in the form of a light yellow oil (341 mg, 79%) by using 2-(4-methoxyphenyloxy) ethyl bromide in the same manner as that of Example 23.

NMR(CDCl3) δ: 1.62–1.90(4H, m), 2.28–2.36(1H, m), 2.70–2.90(2H, m)3.17–3.28(2H, m), 3.36–4.43(1H, m), 3.77 (3H, s), 4.02–4.20(3H, m), 5.26 (1H, d, J=12.3 Hz), 5.33 (1H, d, J=12.3 Hz), 6.72–6.88(7H, m), 7.00–7.15(3H, m), 7.28–7.34(2H, m).

EXAMPLE 34

(R)-5,11-Dihydro-5-[1-[2-(4-methoxyphenyloxy)ethyl]-2-pyrrolidinylmethyl]dibenzo [b,e][1,4]oxazepine Hydrochloride The title compound was obtained in the form of a white solid (yield: 78%) by treating the compound, obtained in Example 33, in the same manner as that of Example 24.

Melting point: 186–191° C.; ESI/Mass: 431 [M+H+]; NMR(CDCl3) δ: 1.90–2.03(1H, m), 2.13–2.23(3H, m), 3.02–3.12(1H, m)3.23–3.32(1H, m), 3.54–3.63(1H, m), 3.70–3.82(1H, m), 3.73(3H, s), 3.83–3.96(1H, m), 4.23(1H, dd, J=8.1, 14.1 Hz), 4.29–4.35(1H, m), 4.53–4.62(1H, ·m), 4.68(1H, dd, J=5.1, 14.1 Hz), 5.21(1H, d, J=12.6 Hz), 5.29(1H, d, J=12.6 Hz), 6.76–6.88(7H, m), 6.98–7.15(3H, m), 7.22–7.32(2H, m).

EXAMPLE 35

(R)-5,11-Dihydro-5-[1-[3-(4-dimethylaminophenyl)propane-1-yl]-2-pyrrolidinylmethyl]dibenzo[b,e][1,4]oxazepine The title compound was obtained in the form of a light yellow oil (yield: 54%) by using 3-(4-dimethylaminophenyl)-1-propyl tosylate in the same manner as that of Example 23.

NMR(CDCl3) δ: 1.60–1.90(6H, m), 2.08–2.20(1H, m), 2.28–2.40(1H, m), 2.48–2.61(2H, m), 2.62–2.78(1H, m), 2.80–2.90(1H, m), 2.90(6H, s), 3.10–3.21(1H, m), 3.41(1H, dd, J=4.2, 13.2 Hz), 4.10(1H, dd, J=3.3, 13.2 Hz), 5.21(1H, d, J=11.7 Hz), 5.30(1H, d, J=11.7 Hz), 6.70(2H, d, 8.4 Hz), 6.75–6.84(3H, m), 6.91–7.07(3H, m), 7.07(2H, d, 8.4 Hz), 7.22–7.32(2H, m).

EXAMPLE 36

(R)-5,11-Dihydro-5-[1-[3-(4-dimethylaminophenyl)propane-1-yl]-2-pyrrolidinylmethyl]dibenzo[b,e][1,4]oxazepine Dihydrochloride The title compound was obtained in the form of a light brown solid (yield: 86%) by treating the compound, obtained in Example 35, in the same manner as that of Example 24.

ESI/Mass: 442 [M+H+]; NMR(CDCl3) δ: 1.50–2.00(4H, m), 2.10–2.20(2H, m), 2.32–2.44(1H, m)2.62–2.68(3H, m), 3.05(6H, s), 3.33–3.46(2H, m), 3.80–3.90(1H, m), 4.19 (1H, dd, J=7.2, 14.1 Hz), 4.59(1H, dd, J=5.1, 14.1 Hz), 5.16(1H, d, J=12.3 Hz), 5.29(1H, d, J=12.3 Hz), 6.81–6.91(3H, m), 6.86(2H, d, J=8.1), 6.96–7.05(2H, m), 7.09(2H, d, J=8.1), 7.20–7.36(3H, m).

EXAMPLE 37

(R)-5,11-Dihydro-5-[1-[3-(3-dimethylaminophenyl) propane-1-yl]-2-pyrrolidinylmethyl]dibenzo[b,e][1,4]oxazepine The title compound was obtained in the form of a light yellow oil (304 mg, 69%) by using 3-(3-dimethylaminophenyl)-1-propyl tosylate in the same manner as that of Example 23.

NMR(CDCl3) δ: 1.60–1.92(6H, m), 2.10–2.20(1H, m), 2.30–2.48(1H, m), 2.56–2.72(3H, m), 2.84–2.96(1H, m), 2.98(6H, s), 3.12–3.18(1H, m), 3.36 (1H, dd, J=10.7, 14.3 Hz), 4.10(1H, dd, J=3.7, 14.3 Hz), 5.24(1H, d, J=13.0 Hz), 5.32(1H, d, J=13.0 Hz), 6.60–6.65(3H, m), 6.76–6.84(3H, m), 6.98–7.36 (6H, m).

EXAMPLE 38

(R)-5,11-Dihydro-5-[1-[3-(3-dimethylaminophenyl) propane-1-yl]-2-pyrrolidinylmethyl]dibenzo[b,e][1,4]oxazepine Dihydrochloride The title compound was obtained in the form of a light brown solid (338 mg, 95%) by treating the compound, obtained in Example 35, in the same manner as that of Example 24.

Melting point: 120–123° C.; ESI/Mass: 442 [M+H+]; NMR(CDCl3) δ: 1.60–2.00(4H, m), 2.00–2.20(2H, m), 2.24–2.62(1H, m)2.70–2.92(3H, m), 3.00–3.22(1H, m), 3.10 (6H, s), 3.33–3.50(2H, m), 4.19 (1H, dd, J=6.7, 16.0 Hz), 4.59(1H, dd, J=6.7, 16.0 Hz), 5.02(1H, d, J=13.7 Hz), 5.11(1H, d, J=13.7 Hz), 6.80–6.96(4H, m), 7.07(2H, t, J=8.1), 7.95(1H, d, J=8.1 Hz), 7.23–7.32(2H, m), 7.40(1H, t, J=8.1), 7.60(1H, d, J=8.1 Hz), 7.83(1H, s).

EXAMPLE 39

(R)-5,11-Dihydro-5-[1-[3-(3-(N-methylaminophenyl)propane-1-yl]-2-pyrrolidinylmethyl]dibenzo[b,e][1,4]oxazepine (R)-5,11-dihydro-5-(2-pyrrolidinylmethyl)dibenzo [b,e][1,4]oxazepine (Preparation Example 1) (280 mg, 1.0 mmol), 3-[3-(N-t-butoxycarbonyl-N-methylamino)phenyl]-1-propyl tosylate (503 mg, 1.2 mmol), sodium carbonate (127 mg, 1.2 mmol) and sodium iodide (30 mg, 0.2 mmol) were added to acetonitrile (15 ml), and the mixture was heated under reflux at 90° C. for 9 hours. The solvent was evaporated under reduced pressure, and the residue was partitioned in ethyl acetate and water. The organic layer was washed with water and then dried over magnesium sulfate. The solvent was evaporated under reduced pressure. The residue was treated by the column chromatography and then eluted with dichloromethane and then with dichloromethane/methanol (50/1) as the eluents. A suitable fraction was collected, the solvent was evaporated under reduced pressure, and the residue was dissolved in dichloromethane. 1.0 ml of 4 M hydrochloride/dioxane was added to the obtained solution, and they were stirred at room temperature for one hour. The solvent was evaporated, and the residue was partitioned in 0.5 M-NaOH and chloroform. The organic layer was dried over magnesium sulfate, and the solvent was evaporated under reduced pressure to obtain the title compound in the form of a light yellow oil (376 mg, 88%).

NMR(CDCl3) δ: 1.60–1.78(4H, m), 1.95(2H, q, J=8.6 Hz) 2.08–2.17(1H, m), 2.28–2.38(1H, m), 2.52–2.72(3H, m), 2.82–2.92(1H, m), 2.86(3H, s), 3.08–3.16(1H, m), 3.60 (1H, dd, J=10.7, 14.3 Hz), 4.09(1H, dd, J=3.7, 14.3 Hz), 5.24(1H, d, J=13.0 Hz), 5.34(1H, d, J=13.0 Hz), 6.45–6.53 (2H, m), 6.58–6.62(1H, m), 6.76–6.85(3H, m), 6.99–7.16 (4H, m), 7.27–7.35(2H, m).

EXAMPLE 40

(R)-5,11-Dihydro-5-[1-[3-(3-dimethylaminophenyl) propane-1-yl]-2-pyrrolidinylmethyl]dibenzo[b,e][1,4]oxazepine Dihydrochloride The title compound was obtained in the form of a white solid (297 mg, 68%) by treating the compound, obtained in Example 39, in the same manner as that of Example 24.

Melting point: 126–129° C.; ESI/Mass: 428 [M+H+]; NMR(CDCl3) δ: 1.85–2.35(6H, m), 2.63–2.78(2H, m), 2.82–2.95(1H, m), 2.97(3H, s), 3.37–3.52(2H, m), 3.70–3.86(2H, m), 4.13(1H, dd, J=8.7, 15.3 Hz), 4.59(1H, dd, J=6.0, 15.3 Hz), 5.18(1H, d, J=14.0 Hz), 5.31(1H, d, J=14.0 Hz), 6.78–6.88(3H, m), 6.99–7.07(3H, m), 7.12–7.32 (5H, m), 7.44–7.50(1H, m), 7.58(1H, s).

Pharmaceutical Formulation Examples will be given below.

PHARMACEUTICAL FORMULATION EXAMPLE 1

The following ingredients were mixed and tableted by an ordinary method to obtain tablets containing 50 mg/tablet of the active ingredient.

| | |
|---|---|
| Compound of Example 2 | 50 mg |
| Lactose | 200 mg |
| Crystalline cellulose | 40 mg |
| Magnesium stearate | 5 mg |

PHARMACEUTICAL FORMULATION EXAMPLE 2

The following ingredients were mixed and the obtained mixture was granulated by an ordinary method to obtain granules.

| | |
|---|---|
| Compound of Example 2 | 50 mg |
| Lactose | 90 mg |
| Corn starch | 60 mg |
| Talc | 30 mg |
| Magnesium stearate | 10 mg |

PHARMACEUTICAL FORMULATION EXAMPLE 3

Tablets were prepared in the same manner as that of Pharmaceutical Formulation Example 1 except that the compound of Example 2 was replaced with the compound of Example 24.

PHARMACEUTICAL FORMULATION EXAMPLE 4

Tablets were prepared in the same manner as that of Pharmaceutical Formulation Example 2 except that the compound of Example 2 was replaced with the compound of Example 24.

The description will be made on the pharmacological tests of the compounds of the present invention.

TEST EXAMPLE 1
In Vitro Calcium Channel-antagonistic Effect (Blood Vessel):

The thoracic aortae were taken out of male Crj:CD rats (8–12 weeks old) and spiral samples were prepared from them. The blood vessel samples were suspended in Tyrode's solution in which a mixed gas (95% of oxygen and 5% of carbon dioxide) was introduced at 37° C. As for the change in tension of each blood vessel, the isometry was recorded on an ink writing recorder through a transducer. The high potassium contraction was caused by changing the nutritive solution from the Tyrode's solution to a potassium-Tyrode's solution (94.6 mM of NaCl, 45.0 mM of KCl, 1.8 mM of $CaCl_2$, 1.04 mM of $MgCl_2$, 0.4 mM of $NaH_2PO_4$, 11.9 mM of $NaHCO_3$, and 5.55 mM of glucose). The high potassium contraction-inhibiting effect of the test compound was determined by 30 minute pretreatment. Compound A described in European Patent No. 0404359A1 was used as a comparative substance. The results of the determination of the calcium channel antagonistic activity were given in terms of the rate of inhibition of the high calcium contraction with $10^{-7}$ M of the test compound. The concentration of the test compound for exhibiting 50% contraction inhibition ($IC_{50}$) is also shown in Table 1. In Table 1, "–" means not determined.

TABLE 1

Calcium channel antagonistic effect (blood vessel)

| Test compound | Inhibition rate (%) (conc.: $10^{-7}$M) | $IC_{50}$ (nM) |
| --- | --- | --- |
| Example 2 | 12 | 255 |
| Example 6 | 24 | — |
| Example 10 | 51 | 57 |
| Example 14 | 41 | 82 |
| Example 19 | 36 | — |
| Example 24 | 31 | 180 |
| Example 38 | 25 | — |
| Compound A | 9 | 530 |

Compound A

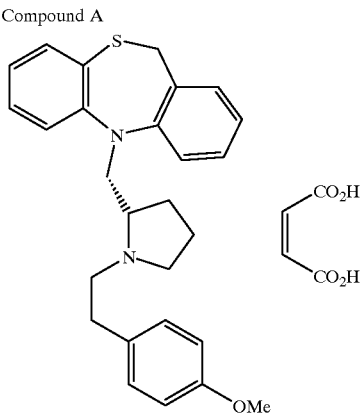

TEST EXAMPLE 2
In Vitro Calcium Channel-antagonistic Effect (Ileum):

The ileum was taken out of male Crj:CD rats (8–12 weeks old) at a position of 3 cm distant from the ileocecal region. The ileum samples were suspended in Tyrode's solution in which a mixed gas (95% of oxygen and 5% of carbon dioxide) was introduced at 37° C. As for the change in tension of the ileum, the isometry was recorded on a ink writing recorder through a transducer. The high potassium contraction was caused by changing the nutritive solution from the Tyrode's solution to a potassium-Tyrode's solution (94.6 mM of NaCl, 45.0 mM of KCl, 1.8 mM of $CaCl_2$, 1.04 mM of $MgCl_2$, 0.4 mM of $NaH_2PO_4$, 11.9 mM of $NaHCO_3$, and 5.55 mM of glucose). The high potassium contraction-inhibiting effect of the test compound was determined by 30 minute pretreatment. Compound A described in European Patent No. 0404359A1 was used as a comparative substance. The results of the determination of the calcium channel antagonistic activity were given in terms of the rate of inhibition of the high calcium contraction with $10^{-7}$ M of the test compound. The concentration of the test compound for exhibiting 50% contraction inhibition ($IC_{50}$) is also shown in Table 2. In Table 2, "–" means not determined.

TABLE 2

Calcium channel antagonistic effect (ileum)

| Test compound | Inhibition rate (%) (conc.: $10^{-7}$M) | $IC_{50}$(nM) |
| --- | --- | --- |
| Example 2 | 62 | 35 |
| Example 6 | 51 | — |
| Example 10 | 87 | 17 |
| Example 14 | 76 | 18 |
| Example 19 | 71 | — |
| Example 24 | 67 | 43 |
| Example 38 | 52 | — |
| Compound A | 48 | 120 |

It is apparent from the results shown in Tables 1 and 2 that the compounds of the present invention have an excellent calcium channel antagonistic effect, and that they are calcium channel antagonists having a particularly high selectivity toward the intestinal tracts.

TEST EXAMPLE 3
Determination of Solubility:

A test compound was suspended in 0.15 M phosphate buffer solution having pH of 7.2 at room temperature. The obtained suspension was vigorously shaken and then left to stand overnight. The insoluble compound was removed by centrifugation, and the concentration of the compound in the supernatant was determined by the high-performance liquid chromatography. The concentration of the compound thus determined was taken as the solubility and shown in Table 3.

TABLE 3

Solubility in neutral buffer solution:

| Test compound | Solubility (mg/ml) |
| --- | --- |
| Example 2 | 0.036 |
| Example 6 | 0.638 |
| Example 8 | 0.116 |
| Example 10 | 0.030 |
| Example 13 | 0.418 |
| Example 14 | 0.056 |
| Example 24 | 0.049 |
| Example 38 | 0.041 |
| Compound A | 0.013 |

It is apparent from the results shown in Table 3 that the compounds of the present invention have a high water solubility. It is expected that when they are orally administered, they are rapidly and easily absorbed. In addition, it is strongly expected that when they are to be used in the form of a liquid preparation, the pharmaceutical preparation can be easily produced.

It is apparent from the Test Examples given above that the compounds of the present invention can exhibit excellent effects as agents for treating and preventing intestinal diseases such as abnormal motor function of digestive tracts, particularly irritable bowel syndrome.

What is claimed is:

1. A compound represented by formula [I-I], or its stereoisomers, pharmacologically acceptable salts or hydrates thereof:

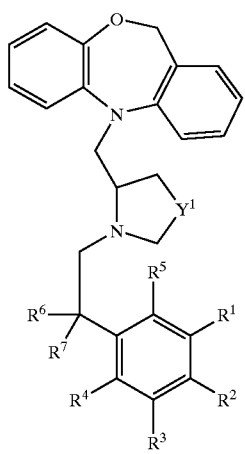

[I-I]

wherein $R^1$ through $R^5$ may be the same or different from one another and they each represent a hydrogen atom, lower alkoxyl group, amino group or alkylamino group with the proviso that at least one of them represents the amino group or alkylamino group;

$R^6$ and $R^7$ may be the same or different from one another and they each represent a hydrogen atom or hydroxyl group, or they together form =O; and $Y^1$ represents a methylene group, sulfur atom or hydroxymethine group.

2. The compound as claimed in claim 1, wherein $R^1$ and $R^2$ may be the same or different from each other, and they each represent a hydrogen atom, amino group or alkylamino group, with the proviso that both $R^1$ and $R^2$ do not represent hydrogen atom at the same time, and $R^3$, $R^4$ and $R^5$ each represent a hydrogen atom.

3. The compound as claimed in claim 1, wherein $Y^1$ represents methylene group.

4. The compound as claimed in claim 1, wherein one of $R^1$ through $R^5$ represents an amino group or alkylamino group, and the remaining is hydrogen atom.

5. The compound as claimed in claim 1, wherein one of $R^1$ through $R^5$ represents an amino group or alkylamino group, the balance is hydrogen atom, and $Y^1$ represents a methylene group.

6. The compound as claimed in claim 1, wherein one of $R^1$ through $R^5$ represents an amino group or alkylamino group, and the remaining is hydrogen atom, and $R^6$ and $R^7$ each represent a hydrogen atom.

7. The compound as claimed in claim 1, wherein one of $R^1$ through $R^5$ represents an amino group or alkylamino group, and the remaining is hydrogen atom, $R^6$ and $R^7$ each represent a hydrogen atom, and $Y^1$ represents a methylene group.

8. The compound as claimed in claim 1, wherein the configuration at the 2-position of the pyrrolidine ring is of R-form.

9. A compound represented by formula [I-II], or its stereoisomers, pharmacologically acceptable salts or hydrates thereof:

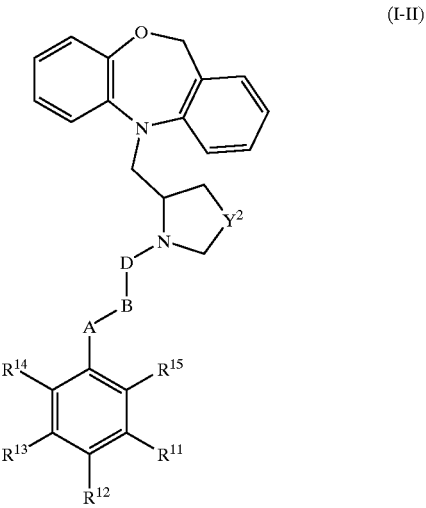

(I-II)

wherein $R^{11}$ through $R^{15}$ may be the same or different from one another and they each represent a hydrogen atom, halogen atom, cyano group, hydroxyl group, lower alkoxyl group, amino group or alkylamino group, or $R^{15}$ and $R^{11}$, $R^{11}$ and $R^{12}$, $R^{12}$ and $R^{13}$ or $R^{13}$ and $R^{14}$ together form —O(CH$_2$)$_n$O— group (n being 1, 2 or 3); $Y^2$ represents a methylene group, sulfur atom or hydroxymethine group; A represents CH$_2$, CHOH, CO or O; B represents CH$_2$ or CHOH; or A—B represents CH=CH; and D represents CH$_2$, CH$_2$—CH$_2$ or CH$_2$—CH$_2$—CH$_2$.

10. The compound as claimed in claim 9, wherein $R^{11}$ and $R^{12}$ may be the same or different from each other and they each represent a hydrogen atom, halogen atom, cyano group, hydroxyl group, lower alkoxyl group, amino group or alkylamino group, $R^{13}$ through $R^{15}$ each represent a hydrogen atom, or $R^{11}$ and $R^{12}$ may together form —O(CH$_2$)$_n$O— group (n being 1, 2 or 3).

11. The compound as claimed in claim 9, wherein $R^{12}$ represents a methoxyl group, and $R^{11}$ and $R^{13}$ through $R^{15}$ each represent a hydrogen atom.

12. The compound as claimed in claim 9, wherein $R^{11}$ represents an amino group or alkylamino group.

13. The compound as claimed in claim 9, wherein $Y^2$ represents a methylene group.

14. The compound as claimed in claim 9, wherein A, B and D each represent CH$_2$.

15. The compound as claimed in claim 9, wherein the configuration at the 2-position of the pyrrolidine ring is of R-form.

16. A pharmaceutical composition comprising a compound represented by formula (I-I), or its stereoisomers, pharmacologically acceptable salts or hydrates thereof:

[I-I]

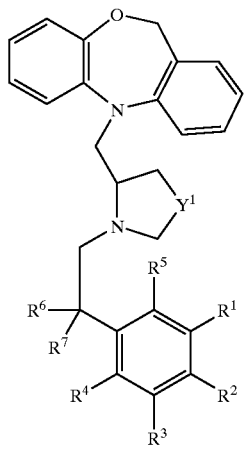

wherein $R^1$ through $R^5$ may be the same or different from one another and they each represent a hydrogen atom, lower alkoxyl group, amino group or alkylamino group with the proviso that at least one of them represents the amino group or alkylamino group;

$R^6$ and $R^7$ may be the same or different from one another and they each represent a hydrogen atom or hydroxyl group, or they together form xO; and $Y^1$ represents a methylene group, sulfer atom or hydroxymethine group as an active ingredient; and a pharmaceutically acceptable excipient, carrier or diluent.

17. A pharmaceutical composition comprising a compound represented by formula (I-II), or its stereoisomers, pharmacologically acceptable salts or hydrates thereof:

(I-II)

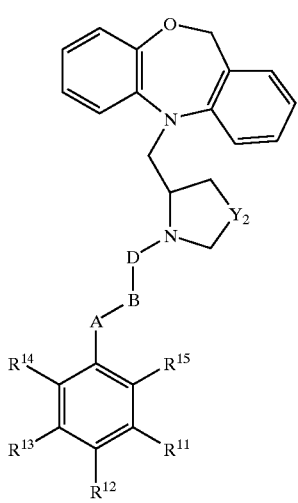

wherein $R^{11}$ through $R^{15}$ may be the same or different from one another and they each represent a hydrogen atom, halogen atom, cyano group, hydroxyl group, lower alkoxyl group, amino group or alkylamino group, or $R^{15}$ and $R^{11}$, and $R^{12}$, $R^{12}$ and $R^{13}$ and $R^{14}$ together form —O(CH$_2$)$_n$O— group (n being 1, 2 or 3); $Y^2$ represents a methylene group, sulfer atom or hydroxymethine group; A represents CH$_2$, CHOH, CO or O; B represents CH$_2$ or CHOH; or A-B represents CHxCH; and D represents Ch$_2$, CH$_2$—CH$_2$ or CH$_2$—CH$_2$—CH$_2$ as an active ingredient; and a pharmaceutically acceptable excipient, carrier or diluent. claimed in claim 9 as an active ingredient; and a pharmaceutically acceptable excipient, carrier or diluent.

18. A method for treating abnormal motor function of digestive tracts, which comprises administering, to a subject in need thereof, a compound represented by formula (I-I), or its stereoisomers, pharmacologically acceptable salts or hydrates thereof:

[I-I]

wherein $R^1$ through $R^5$ may be the same or different from one another and they each represent a hydrogen atom, lower alkoxyl group, amino group or alkylamino group with the proviso that at least one of them represents the amino group or alkylamino group;

$R^6$ and $R^7$ may be the same or different from one another and they each represent a hydrogen atom or hydroxyl group, or they together form xO; and $Y^1$ represents a methylene group, sulfer atom or hydroxymethine group as an active ingredient.

19. A method for treating abnormal motor function of digestive tracts, which comprises administering, to a subject in need thereof, a compound represented by formula (I-II), or its stereoisomers, pharmacologically acceptable salts or hydrates thereof:

(I-II)

wherein $R^{11}$ through $R^{15}$ may be the same or different from one another and they each represent a hydrogen atom, halogen atom, cyano group, hydroxyl group, lower alkoxyl group, amino group or alkylamino group, or $R^{15}$ and $R^{11}$, $R^{11}$ and $R^{12}$, $R^{12}$ and $R^{13}$ or $R^{13}$ and $R^{14}$ together form —O(CH$_2$)$_n$O— group (n being 1, 2 or 3); $Y^2$ represents a methylene group, sulfer atom or hydroxymethine group; A represents CH$_2$, CHOH, CO or O; B represents CH$_2$ or CHOH; or A-B represents CH×CH; and D represents CH$_2$, CH$_2$—CH$_2$ or CH$_2$—CH$_2$—CH$_2$ as an active ingerdient.

20. The composition as claimed in claim 16, wherein $R^1$ and $R^2$ may be the same or different from each other, and they each represent a hydrogen atom, amino group or alkylamino group, with the proviso that both $R^1$ and $R^2$ do not represent hydrogen atom at the same time, and $R^3$, $R^4$ and $R^5$ each represent a hydrogen atom.

21. The composition as claimed in claim 16, wherein one of $R^1$ through $R^5$ represents an amino group or alkylamino group, and the remaining is hydrogen atom, $R^6$ and $R^7$ each represent a hydrogen atom, and $Y^1$ represents a methylene group.

22. The composition as claimed in claim 16, wherein the configuration at the 2-position of the pyrrolidine ring is of R-form.

23. The composition as claimed in claim 17, wherein $R^{11}$ and $R^{12}$ may be the same or different from each other and they each represent a hydrogen atom, halogen atom, cyano group, hydroxyl group, lower alkoxyl group, amino group or alkylamino group, $R^{13}$ through $R^{15}$ each represent a hydrogen atom, or $R^{11}$ and $R^{12}$ may together form —O(CH$_2$)$_n$O— group (n being 1, 2 or 3).

24. The composition as claimed in claim 17, wherein A, B and D each represent CH$_2$.

25. The composition as claimed in claim 17, wherein the configuration at the 2-position of the pyrrolidine ring is of R-form.

26. The method as claimed in claim 18, wherein $R^1$ and $R^2$ may be the same or different from each other, and they each represent a hydrogen atom, amino group or alkylamino group, with the proviso that both $R^1$ and $R^2$ do not represent hydrogen atom at the same time, and $R^3$, $R^4$ and $R^5$ each represent a hydrogen atom.

27. The method as claimed in claim 18, wherein one of $R^1$ through $R^5$ represents an amino group or alkylamino group, the balance is hydrogen atom, and $Y^1$ represents a methylene group.

28. The method as claimed in claim 18, wherein one of the $R^1$ through $R^5$ represents an amino group or alkylamino group, and the remaining is hydrogen atom, and $R^6$ and $R^7$ each represent a hydrogen atom.

29. The method as claimed in claim 18, wherein the configuration at the 2-position of the pyrrolidine ring is of R-form.

30. The method as claimed in claim 18, wherein said treating comprises treating at least one selected from the group consisting of irritable bowel syndrome, irregular bowel movement and abdominal pain.

31. The method as claimed in claim 18, wherein said treating comprises treating at least one selected from the group consisting of irregular bowel movement and abdominal pain.

32. The method as claimed in claim 31, wherein said treating comprises treating irregular bowel movement.

33. The method as claimed in claim 31, wherein said treating comprises treating abdominal pain.

34. The method as claimed in claim 19, wherein $R^{11}$ and $R^{12}$ may be the same or different from each other and they each represent a hydrogen atom, halogen atom, cyano group, hydroxyl group, lower alkoxyl group, amino group or alkylamino group, $R^{13}$ through $R^{15}$ represent a hydrogen atom, or $R^{11}$ and $R^{12}$ may together form —O(CH$_2$)$_n$O— group (n being 1, 2 pr 3).

35. A method for treating irritable bowel syndrome, which comprises administering, to a subject in need thereof, a compound represented by formula (I-I), or its stereoisomers, pharmacologically acceptable salts or hydrates thereof:

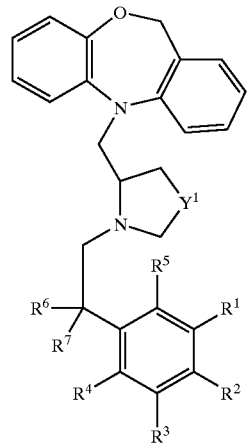

[I-I]

wherein $R^1$ through $R^5$ may be the same or different from one another and they each represent a hydrogen atom, lower alkoxyl group, amino group or alkylamino group with the proviso that at least one of them represents the amino group or alkylamino group;

$R^6$ and $R^7$ may be the same or different from one another and they each represent a hydrogen atom or hydroxyl group, or they together form ×O; and $Y^1$ represents a methylene group, sulfer atom or hydroxymethine group as an active ingredient.

36. The method as claimed in claim 35 wherein $R^1$ and $R^2$ may be the same or different from each other, and they each represent a hydrogen atom, amino group or alkylamino group, with the provisio that both $R^1$ and $R^2$ do not represent hydrogen atom at the same time, and $R^3$, $R^4$ and $R^5$ each represent a hydrogen atom.

37. The method as claimed in claim 35, wherein $Y^1$ represents methylene group.

38. The method as claimed in claim 25, wherein one of $R^1$ through $R^5$ represents an amino group or alkylamino group, and the remaining is hydrogen atom.

39. The method as claimed in claim 35, wherein one of $R^1$ through $R^5$ represents an amino group or alkylamino group, the balance is hydrogen atom, and $Y^1$ represents a methylene group.

40. The method as claimed in claim 35, wherein one of $R^1$ through $R^5$ represents an amino group or alkylamino group, and the remaining is hydrogen atom, and $R^6$ and $R^7$ each represent a hydrogen atom.

41. The method as claimed in claim 35, wherein one of $R^1$ through $R^5$ represents an amino group or alkylamino group, and the remaining is hydrogen atom, $R^6$ and $R^7$ each represent a hydrogen atom, and $Y^1$ represents a methylene group.

42. The method as claimed in claim 35, wherein the configuration at the 2-position of the pyrrolidine ring is of R-form.

43. A method for treating irritable bowel syndrome, which comprises administering, to a subject in need thereof, a compound represented by formula (I-II), or its stereoisomers, pharmacologically acceptable salts or hydrates thereof:

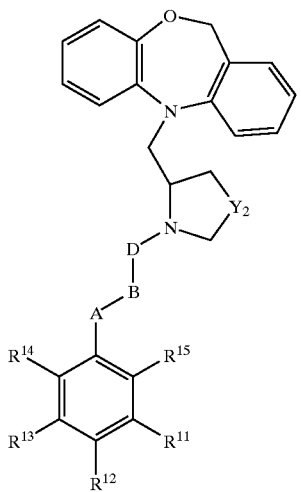

(I-II)

wherein $R^{11}$ through $R^{15}$ may be the same of different from one another and they each represent a hydrogen atom, halogen atom, cyano group, hydroxyl group, lower alkoxyl group, amino group or alkylamino group, or $R^{15}$ and $R^{11}$, $R^{11}$ and $R^{12}$, $R^{12}$ and $R^{13}$ and $R^{14}$ together form —O(CH$_2$)$_n$O— group (n being 1, 2 or 3); $Y^2$ represents a methylene group, sulfer atom or hydroxymethine group; A represents CH$_2$, CHOH, CO or O; B represents CH$_2$ or CHOH; or A-B represents CH×CH; and D represents CH$_2$, CH$_2$—CH$_2$ or CH$_2$—CH$_2$—CH$_2$ as an active ingredient.

44. The method as claimed in claim 43, wherein $R^{11}$ and $R^{12}$ may be the same or different from each other and they each represent a hydrogen atom, halogen atom, cyano group, hydroxyl group, lower alkoxyl group, amino group or alkylamino group, $R^{13}$ through $R^{15}$ each represent a hydrogen atom, or $R^{11}$ and $R^{12}$ may together form —O(CH$_2$)$_n$O— group (n being 1, 2 or 3).

45. The method as claimed in claim 43, wherein $R^{12}$ represents a methoxyl group, and $R^{11}$ and $R^{13}$ through $R^{15}$ each represent a hydrogen atom.

46. The method as claimed in claim 43, wherein $R^{11}$ represents an amino group or alkylamino group.

47. The method as claimed in claim 43, wherein $Y^2$ represents a methylene group.

48. The method as claimed in claim 43, wherein A, B and D each represent CH$_2$.

49. The method as claimed in claim 43, wherein the configuration at the 2-position of the pyrrolidine ring is of R-form.

* * * * *